United States Patent
Kumar et al.

(10) Patent No.: US 10,254,287 B2
(45) Date of Patent: Apr. 9, 2019

(54) PROTEIN FLUORESCENT NANOPARTICLES AND METHODS OF SYNTHESIS THEREOF

(71) Applicant: University of Connecticut, Farmington, CT (US)

(72) Inventors: Challa Vijaya Kumar, Ashford, CT (US); Bobbi Shanyelle Stromer, Willimantic, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 15/216,420

(22) Filed: Jul. 21, 2016

(65) Prior Publication Data

US 2017/0023580 A1    Jan. 26, 2017

Related U.S. Application Data

(60) Provisional application No. 62/194,926, filed on Jul. 21, 2015.

(51) Int. Cl.

| | |
|---|---|
| G01N 33/58 | (2006.01) |
| G01N 21/64 | (2006.01) |
| G01N 25/48 | (2006.01) |
| C07K 1/13 | (2006.01) |
| G01N 33/84 | (2006.01) |
| G01N 33/50 | (2006.01) |
| G01N 21/19 | (2006.01) |
| G01N 33/533 | (2006.01) |
| G01N 33/543 | (2006.01) |

(52) U.S. Cl.
CPC ............ *G01N 33/587* (2013.01); *C07K 1/13* (2013.01); *G01N 21/19* (2013.01); *G01N 21/6428* (2013.01); *G01N 25/48* (2013.01); *G01N 33/5005* (2013.01); *G01N 33/533* (2013.01); *G01N 33/54346* (2013.01); *G01N 33/582* (2013.01); *G01N 33/84* (2013.01); *G01N 2021/6417* (2013.01); *G01N 2021/6432* (2013.01); *G01N 2021/6439* (2013.01); *G01N 2333/765* (2013.01); *G01N 2333/904* (2013.01); *G01N 2333/908* (2013.01); *G01N 2333/92* (2013.01); *G01N 2333/936* (2013.01)

(58) Field of Classification Search
None
See application file for complete search history.

(56) References Cited

U.S. PATENT DOCUMENTS

2006/0145091 A1* 7/2006 Patel .................. G01T 1/04
250/474.1
2009/0004278 A1  1/2009 Aimi et al.
2013/0030282 A1* 1/2013 Margel ................ A61K 49/0002
600/411
2014/0328764 A1* 11/2014 Tang ................... C09K 11/06
424/9.6
2015/0004242 A1* 1/2015 Wang .................. A61K 9/5169
424/499

FOREIGN PATENT DOCUMENTS

WO        2007086613        8/2007

OTHER PUBLICATIONS

Cui et al., Mater. Chem. Front. 1:387-393 (2017).*
Ming et al., Biomater., 34(32):1-22 (2013).*
Zhao et al., Internat. J. Nanomedic., 14(9):2149-2156 (2014).*
Taheri et al., Internat. J. Nanomedic., 6:1863-1874 (2011).*
Zhang et al., Curr. Protoc. Cytom., 12.27:1-28 (2012).*
Biasi et al., Mater. Res., 12(2):225-227 (2009).*
Xie et al (JACS, 131:888-889 (2009).*
Bao et al., ACS Appl. Mater. Interfaces, 6:11129-11135 (2014).*
Bu et al., Nature Comm., 5(3799)1-8 (2012).*
Chan et al., Anal. Chem., 84:8952-8956 (2012).*
Chen et al., Biomacromol., 12:2552-2561 (2011).*
Cohen et al., J. Nanobiotech., 10(36):1-8 (2012).*
Hellriegel et al., J. R. Soc. Interface, 6:S3-S14 (2009).*
Hoffmann et al., ACS Nano., 7(8):6674-6684 (2013).*
Khandelia et al., Mater. Views, pp. 1-7 (2015).*
Khullar et al., J. Phys. Chem. C, 116:8834-8843 (2012).*
Kim et al., Acta Biomater., 8(7):2476-2482 (2012).*
Langer et al., Internat. J. Pharma., 257:169-180 (2003).*
Lewis et al., Nat. Med., 12(3):354-360 (2006).*
Li et al., Nanotech., 18:1-7 (2007).*
Liu et al., Part. Part. Syst. Charact., 32:749-755 (2015).*
Niknejad et al., Iran. J. Pharma. Res., 14(2):385-394 (2015).*
Ng et al., Chem. Rev., 115:11012-11042 (2015).*
Paik et al., Food Chem., 141:695-701 (2013).*
Park et al., ACS Nano., 5(4):2483-2492 (2011).*
Qu et al., J. Nanomater., 784097:1-23 (2015).*
Swierczewska et al., Phys. Chem. Chem. Phys., 13(21): 9929-9941 (2011).*
Xu et al., Nanoscale, 6:1515-1524 (2014).*
Zhang et al., ACS Appl. Mater. Interfaces, 5:8710-8717 (2013).*
Zhong et al., ACS Appl. Mater. Interfaces, 6:19465-19470 (2014).*
Gai et al., Nanoscale, 4:6041-6049 (2012) (Year: 2012).*
Deshapriya,Doctoral Dissertation, (2014) (Year: 2014).*
Li et al., Sci. Rep., 5(8492):1-7 (2015) (Year: 2015).*
Ma et al, "A Biocompatible and Biodegradable Protein Hydrogel with Green and Red Autofluorescence: Preparation, Characterization and in Vivo Biodegradation Tracking and Modeling," (2016) 6,19370.
Yu et al., "Spray freezing into liquid nitrogen for highly stable protein nanostructured microparticles," (2004) Eur. J. Pharm. Biopharm. 58, 529-537.
Alkilany et al., "Cellular uptake and cytotoxicity of gold nanorods: molecular origin of cytotoxicity and surface effects," (2009) Small 5, 701-708.

(Continued)

*Primary Examiner* — Thomas J. Visone
(74) *Attorney, Agent, or Firm* — Michael Best & Friedrich LLP

(57) ABSTRACT

Disclosed herein are stable and versatile protein nanoparticles having a range of tunable fluorescent properties. Such nanoparticles may find utility in biological imaging. Methods of synthesis of such nanoparticles are also disclosed.

16 Claims, 29 Drawing Sheets
(24 of 29 Drawing Sheet(s) Filed in Color)

(56) References Cited

OTHER PUBLICATIONS

Bertorelle et al., "Fluorescence-modified superparamagneticnanoparticles: intracellular uptake and use in cellular imaging," (2006) Langmuir 22, 5385-5391.
Bradburne et al., "Cytotoxicity of Quantum Dots Used for in Vitro Cellular Labeling: Role of QD Surface Ligand, Delivery Modality, Cell Type, and Direct Comparison to Organic Fluorophores," (2013) Bioconjugate Chem. 24, 1570-1583.
Chattopadhyay et al., "Protein nanoparticles formation by supercritical antisolvent with enhanced mass transfer," (2002) AIChE J. 48, 235-244.
Costantino et al., "Protein spray-freeze drying. Effect of atomization conditions on particle size and stability," (2000) Pharm. Res. 17, 1374-1383.
De La Fuente et al., "Tat peptide as an efficient molecule to translocate gold nanoparticles into the cellnucleus," (2005) Bioconj. Chem. 16, 1176-1180.
Deshapriya et al., "Fluorescent, Bioactive Protein Nanoparticles (Prodots) for Rapid, Improved Cellular Uptake", Article (2015) 26, pp. 396-404.
Deshapriya et al., "Fluorescent, Bioactive Protein Nanoparticles (Prodots) for Rapid, Improved Cellular Uptake", Article (2015) 26, Supporting Information (ESI) pp. 1-18.
Park, et al. ,"White-Emitting Conjugated Polymer Nanoparticles with Cross-Linked Shell for Mechanical Stability and Controllable Photometric Properties in Color-Conversion LED Applications," (2011) 2483-2492.
Elzoghby et al., "Albumin-based nanoparticles as potential controlled release drugdelivery systems," J. Controlled Release (2012) 157, 168-182.
Gulseren et al., "Zinc incorporation capacity of whey protein nanoparticles prepared with desolvation with ethanol," (2012) Food Chem. 135, 770-774.
Keita et al., Construction of multi-layered white emitting organic nanoparticles by clicking polymers (2015) 3, 10277-10284.
Tai et al., Nearly warm white-light emission of silicon-rich amorphous silicon carbide (2015) 5, 105239-105247.
Zhou et al., "Taurine Boosts Cellular Uptake of Small D-Peptides for Enzyme-Instructed Intracellular Molecular Self-Assembly," Am. Chem. Soc. (2015) 137, 10040-10043.
Zhi et al., "White emission magnetic nanoparticles as chemosensors for sensitive colorimetric and ratiometric detection, and degradation of ClO- and SCN- in aqueous solutions based on a logic gate approach," Nanoscale (2015) 7, 11712-11719.
Lee et al., "Nano spray drying: A novel method for preparing proteinnanoparticles for protein therapy," Int. J. Pharm. (2011) 403, 192-200.
Montalvo et al., "Formation of spherical protein nanoparticles without impacting protein integrity," Nanotechnology (2008) 19, 465103.
Muhrer et al., "Precipitation of lysozyme nanoparticles from dimethyl sulfoxide using carbon dioxide as antisolvent," Biotechnol. Prog. (2003) 19, 549-556.
Popovic et al., "A nanoparticle size series for in vivo fluorescence imaging," Angew. Chem., Int. Ed. (2010) 49, 8649-8652.
Pramanik et al., "Synchonous Tricolor Emission-Based White Light from Quantum Dot Complex," J. Phys. Chem. Lett. (2015) 6, 1270-1274.
Qin et al., "Biocompatible nanoparticles with aggregation-induced emission characteristics as far-red/near-infrared fluorescent bioprobes for in vitro and in vivo imaging applications," Adv. Funct. Mater (2012) 22, 771-779.
Stromer, et al., "Multi-Colored and White Emitting Fluorescent Protein Nano Particles (nanoProteos) for Imaging" (2016) 25 pages.
Stromer, et al., "White Emitting Protein Nanoparticles for Cell-entry and pH Sensing" paper (2017) 17 pages.
Niu et al., "Ratiometric Emission Fluorescent pH Probe for Imaging of Living Cells in Extreme Acidity," (2015) 87, 27880-02793.

\* cited by examiner

PROTEIN FLUORESCENT NANOPARTICLES AND METHODS OF SYNTHESIS THEREOF

CROSS-REFERENCE TO RELATED APPLICATIONS

This application claims the benefit of U.S. Provisional Patent Application No. 62/194,926 filed Jul. 21, 2015, the entire contents of which are incorporated herein by reference.

STATEMENT OF GOVERNMENT INTEREST

This invention was made with government support under grant number DMR-1441879 awarded by the National Science Foundation. The government has certain rights in the invention.

TECHNICAL FIELD

The present disclosure relates to stable and versatile protein nanoparticles having a range of tunable fluorescent properties. Such nanoparticles may find utility in biological imaging. Methods of synthesis of such nanoparticles are also disclosed.

BACKGROUND OF THE INVENTION

Quantum dots are nanosized particles that can be synthesized using toxic elements, such as cadmium, arsenic and others. Quantum dots have been explored for a variety of electronic and biological applications. Their toxicity, however, is restricting wide-spread application in biology. While less toxic elements have been used, such as gold, silver or silica, their manufacture for biological purposes requires the use of biocompatible coatings.

SUMMARY OF THE INVENTION

Disclosed herein is a simple synthesis for protein fluorescent nanoparticles (PNPs) in which nanoparticles are formed from ordinary, edible, proteins via crosslinking with a crosslinking agent, either before or after linking the dyes to the protein. The direct formation of protein nanoparticles with a fluorescent tag either incorporated within or linked to the external surface of the particle may provide a less expensive and more flexible approach for producing non-toxic and biocompatible, biodegradable nanoparticles for biological/cell imaging.

In one aspect, disclosed is a method of synthesizing a protein fluorescent nanoparticle, the method comprising:
  labeling a protein with a fluorescent dye reagent; and
  crosslinking the protein with a crosslinking agent,
  to thereby form the protein fluorescent nanoparticle,
  wherein the protein is labeled with the fluorescent dye either before or after the crosslinking step.

In another aspect, disclosed is a protein fluorescent nanoparticle prepared by a method described herein.

In another aspect, disclosed is a method of imaging a cell, comprising:
  contacting the cell with a protein fluorescent nanoparticle prepared according to a method described herein; and
  detecting the protein fluorescent nanoparticle in the cell.

In another aspect, disclosed is a method of detecting pH in a sample, comprising:
  contacting the sample with a white-emitting protein fluorescent nanoparticle prepared according to the method of any one of claims 8-12; and
  detecting emission from the white-emitting protein fluorescent nanoparticle in the sample over a range of pH values from about 2 to about 11.

In another aspect, disclosed is a method of sensing temperature in a sample, comprising:
  contacting the sample with a white-emitting protein fluorescent nanoparticle prepared according to the method of any one of claims 8-12; and
  detecting emission from the white-emitting protein fluorescent nanoparticle in the sample over a range of temperatures from about 20° C. to about 80° C.

In another aspect, disclosed is a method of synthesizing a protein fluorescent nanoparticle, the method comprising:
  crosslinking a protein with a crosslinking agent to form protein nanoparticles; and
  adding a metal-containing reagent to the protein nanoparticles, to thereby form the protein fluorescent nanoparticles.

Other aspects of the disclosure will become apparent in view of the following description and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
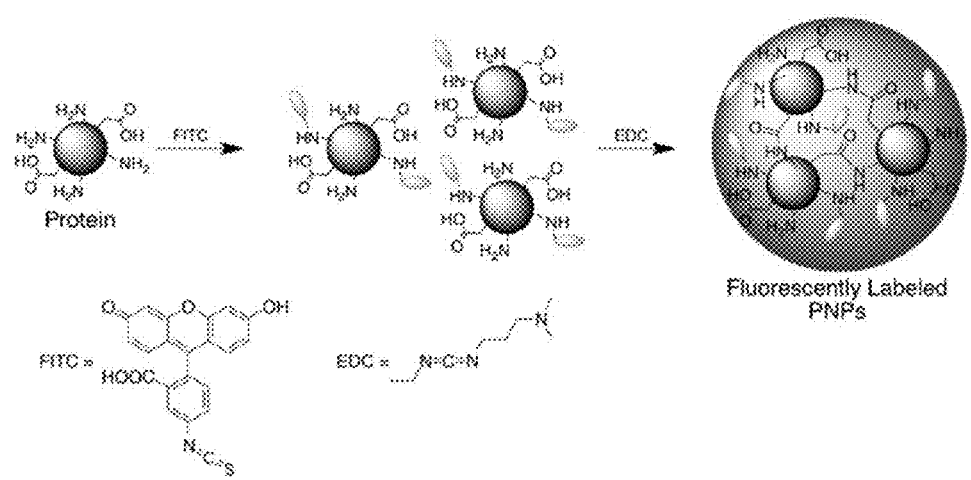
FIG. 1 shows an exemplary synthesis of PNPs by first labeling a protein with fluorescein isothiocyanate followed by crosslinking of the resulting protein clusters with a carbodiimide, EDC.
Figure 2:
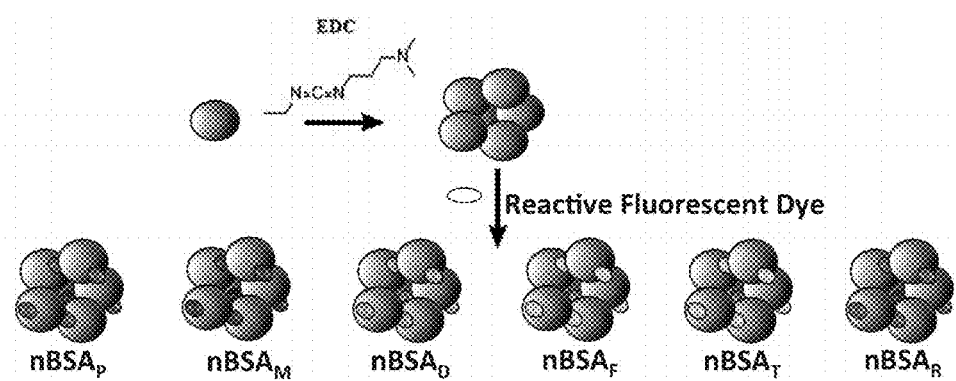
FIG. 2 shows an exemplary synthesis of PNPs by first crosslinking a protein with EDC and subsequently labeling the crosslinked proteins with fluorescent dye reagents.

Disclosed herein are protein fluorescent nanoparticles (PNPs) and a simple method of synthesis thereof. Functional groups on enzymes and proteins can be chemically linked using well-known chemical conjugation reagents to form protein-based nanoparticles of controllable sizes. These protein nanoparticles can then be labeled with one or more dyes to make them colored and/or fluorescent. Nanoparticles of several colors and nanoparticles capable of white light emission can be produced. External linkage of dyes to nanoparticles can be more consistent and reproducible than physical incorporation of dyes within the protein nanoparticles. In addition, suitable combinations of linked fluorescent dyes can produce protein nanoparticles that emit white light or any other desired color or combinations of colors.

Fluorescent dyes having a wide range of discrete excitation and emission wavelengths are available. This flexibility combined with the biocompatibility of the disclosed protein nanoparticles make such particles excellent substitutes for previously known quantum dots in cellular imaging and other biological applications. Further advantages of the disclosed fluorescent nanoparticles include that the particles are both biocompatible and biodegradable, nanoparticles are characterized as having rapid cellular uptake under chemical control or triggers, and nanoparticles have no blinking and may therefore be better than quantum dots. In addition, it is inexpensive and simple to scale up the synthesis of the particles. Still further advantages include discretely tunable absorption wavelengths and independently tunable emission wavelengths, and the nanoparticles are highly stable and storable at room temperature, capable of being shipped for long distances without cooling and without deterioration of their function or characteristics.

While described herein for certain examples, the disclosed method is a general approach for the production of protein nanoparticles from a variety of different proteins and dyes/metal complexes or pigments by a variety of chemical conjugation reactions.

It is an object of the disclosed technology to provide nanoparticles of tunable size. The synthesis allows for controllable sizes and size distributions of protein nanoparticles.

It is an object of the disclosed technology to provide nanoparticles of controllable and tunable color and tunable fluorescence. Different dyes spanning the entire color spectrum are selected and attached to proteins before or after particle formation.

It is an object of the disclosed technology to provide nanoparticles of tunable emission. Selecting and using different fluorescent or phosphorescent dyes or phosphorescent Au nanoparticles, allowed tuning of the emission wavelengths as well as the corresponding luminescent state lifetimes over a wide range.

It is an object of the disclosed technology to provide nanoparticles in which protein structure is retained fully or to a large extent. These novel protein nanoparticles retained the secondary structure of the protein to a significant extent and also produced induced circular dichroism bands for the bound dyes.

Nanoparticles derived from one or more enzymes as disclosed herein displayed significant retention of their enzymatic activities.

It is an object of the disclosed technology to provide nanoparticles characterized by effective cellular uptake: Protein nanoparticles synthesized to comprise glucose oxidase have shown excellent uptake by cancer cells in the presence of added glucose. Furthermore, the addition of glucose oxidase nanoparticle or glucose oxidase enzyme to the cell media containing glucose triggered the uptake of other nanoparticles or protein nanoparticles into the cell.

It is a further object of the disclosed technology to provide nanoparticles characterized by effective cellular uptake without glucose oxidase or glucose oxidase nanoparticle to the cell media. These particles are modified with a natural amino acid, taurine, and taurine coating on the particles triggered the uptake by a variety of cell lines (human or non-human).

Also disclosed herein are methods of making white light emitting protein nanoparticles for multi-color imaging. Labeling with different dyes or with a mixture of dyes resulted in multi-colored nanoparticles which emitted any of several different, specific colors or which emitted white light, depending on the specific dye or groups of dyes selected and added to the nanoparticles.

Also disclosed herein are methods of pH sensing with white light emitting protein nanoparticles by multi-color imaging over a wide pH range of 2 to 11. Particles trapped in different sub-cellular compartments emitted in distinctly different colors, reflecting on their local environments, such as pH.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The terms "first," "second," and the like used herein do not necessarily denote any order, quantity, or relative importance, but can rather be used to distinguish one element from another.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

As used herein, certain fluorescent dyes and fluorescent dye reagents are abbreviated with a single letter, as further described in the specification and examples. "W" denotes white light, and may be further identified by a specified excitation wavelength that produces white fluorescence emission. For example, a subscript "W254" indicates that the nanoparticle emits white fluorescence upon excitation at 254 nm.

As used herein, the abbreviation "n" before the name of a protein or an abbreviation thereof indicates that the protein is in the form of nanoparticles. The protein fluorescent nanoparticles are specified as "n(protein)" to indicate the protein from which the particle has been synthesized. For example, "nBSA" refers to nanoparticles of BSA prepared according to methods disclosed herein, and "nGO" refers to nanoparticles of glucose oxidase prepared according to methods disclosed herein. Additionally, additional abbreviations in subscript or following a hyphen indicate the fluorescent dye used to label the nanoparticles As used herein, the term "GlowDot" is another term for a protein fluorescent nanoparticle prepared by a method disclosed herein. "GlowDot#" as used herein indicates a protein fluorescent nanoparticle where # is the excitation wavelength of the dye used or the excitation wavelength used (e.g., for white fluorescence).

All methods described herein can be performed in any suitable order unless otherwise indicated herein or otherwise clearly contradicted by context. The use of any and all examples, or exemplary language (e.g., "such as"), is intended merely to better illustrate the invention and does not pose a limitation on the scope of the invention or any embodiments unless otherwise claimed.

Chemical compounds are described using standard nomenclature. Unless defined otherwise, all technical and scientific terms used herein have the same meaning as is commonly understood by one of skill in the art to which this invention belongs.

2. METHODS OF SYNTHESIZING PROTEIN FLUORESCENT NANOPARTICLES

Protein-based nanoparticles have previously been prepared by freeze-drying, supercritical fluid technology, spray-drying, desolvation, and enzymatic crosslinking. Most of these methods use organic solvents, drying, or dehydration, which may damage the delicate structures of proteins. Furthermore, while supercritical fluid methods use mild conditions, they primarily produce particles in the 1-10 μm size range, with a wide size distribution and they have little to no control over particle size or size distribution. The method of synthesizing nanoparticles described herein can produce small nano-particles (<50 nm), with narrow size distribution, high stability, a high degree of retention of biological activity/structure, with control over their size as well as uptake by cells.

In one aspect, disclosed is a method for synthesizing protein fluorescent nanoparticles, the method comprising: labeling a protein with a fluorescent dye reagent; and crosslinking the protein with a crosslinking agent, to thereby form the protein fluorescent nanoparticle, wherein the protein is labeled with the fluorescent dye either before or after the crosslinking step. In some embodiments, the protein is labeled with the fluorescent dye reagent before the crosslinking step. In some embodiments, the protein is labeled with the fluorescent dye reagent after the crosslinking step.

For example, the protein-based nanoparticles can be prepared by coupling an amino acid side chain on a protein (e.g., an amino group of a lysine residue) with a fluorescent dye reagent, followed by controlled aggregation of the proteins, followed by crosslinking the protein units (see FIG. 1). The protein-based nanoparticles can also be prepared by crosslinking the protein units, followed by coupling an amino acid side chain on a protein (e.g., an amino group of a lysine residue) with a fluorescent dye reagent. Nanoparticle formation can be monitored using various techniques such as dynamic light scattering, gel electrophoresis, and transmission electron microscopy. Reaction conditions can be optimized to consume all of the free protein, while producing particles of a desired size. Once desired sizes are achieved, the particle formation can be quenched, e.g., by adding a carbonate buffer. The resulting nanoparticles can be purified using techniques such as dialysis, centrifugation and/or filtration.

In another aspect, disclosed is a method of synthesizing a protein fluorescent nanoparticle, the method comprising: providing a solution comprising a protein and a metal-containing reagent; forming a metal nanocluster from the metal-containing reagent; and adding a crosslinking agent to crosslink the protein, to thereby form the protein fluorescent nanoparticles.

In another aspect, disclosed is a method of synthesizing a protein fluorescent nanoparticle, the method comprising:

crosslinking a protein with a crosslinking agent to form protein nanoparticles; and adding a metal-containing reagent to the protein nanoparticles, to thereby form the protein fluorescent nanoparticles.

The ability to use multiple different fluorescent dyes, or a combination of fluorescent dyes with metal nanoclusters, provides the ability to use multi-mode, orthogonal sensing.

Aspects of the disclosed methods are described in further detail below.

a. Proteins

The methods of synthesizing protein fluorescent nanoparticles can be carried out using a variety of proteins. In some embodiments, the protein is selected from the group consisting of bovine serum albumin, glucose oxidase, horseradish peroxidase, catalase, lipase, hemoglobin, and lysozyme, and any combination thereof. In some embodiments, the protein is bovine serum albumin. The protein can itself be fluorescent, or it can be non-fluorescent. For example, the protein may be fluorescent based on fluorescence from tryptophan amino acids in the protein.

Other suitable proteins having sufficient numbers of accessible amine and carboxyl functional groups can also be used in the disclosed methods.

b. Crosslinking Agents

The methods of synthesizing the PNPs can be carried out using a variety of crosslinking agents to crosslink the proteins, either before or after fluorescent labeling. Any suitable crosslinker can be used, including homobifunctional crosslinkers (having identical reactive groups at either end of a spacer arm) and heterobifunctional crosslinkers (having different reactive groups at either end). Typical reactive groups at each end of a crosslinker include N-hydroxysuccinimidyl esters, imidoesters, maleimides, pyridyldithiols, haloacetyls, azides, diazirines, carbodiimides, and isocyanates. Exemplary crosslinkers include the carbodiimides, such as 1-ethyl-3-(3-dimethylaminopropyl) carbodiimide (EDC or EDAC), N,N'-dicyclohexylcarbodiimide (DCC), and N,N'-diisopropylcarbodiimide (DIC). Carbodiimide couplings may be conducted in the further presence of N-hydroxysuccinimide or N-hydroxysulfosuccinimide, which may improve the efficiency of carbodiimide coupling reactions. Other crosslinkers include amine-to-amine crosslinkers such as disuccinimidyl glutarate (DSG), disuccinimidyl suberate (DSS), bis(2-(succinimidooxycarbonyloxy)ethyl)sulfone (BSOCOES), dimethyl suberimidate (DMS), 1,5-difluoro-2,4-dinitrobenzene (DFDNB), dithiobis(succinimidyl propionate) (DSP), tris-(succinimidyl)aminotriacetate (TSAT), dimethyl pimelimidate (DMP), bis(sulfosuccinimidyl)suberate (BS3), ethylene glycol bis (succinimidyl succinate) (EGS), ethylene glycol bis (sulfosuccinimidyl succinate) (sulfo-EGS), disuccinimidyl tartrate (DST), dimethyl 3,3'-dithiobispropionimidate (DTBP), PEGylated bis (sulfosuccinimidyl)suberate (e.g., BS(PEG)5 and BS(PEG)9), 3,3'-dithiobis(sulfosuccinimidyl propionate) (DTSSP), and dimethyl adipimidate (DMA).

Other crosslinkers include amine-to-sulfhydryl crosslinkers such as sulfo-SIAB (sulfosuccinimidyl (4-iodoacetyl)aminobenzoate), SM(PEG)6 (PEGylated, long-chain SMCC crosslinker), SMPT (4-succinimidyloxycarbonyl-alpha-methyl-α(2-pyridyldithio)toluene), SIAB (succinimidyl (4-iodoacetyl)aminobenzoate), sulfo-SMCC (sulfosuccinimidyl 4-(N-maleimidomethyl)cyclohexane-1-carboxylate), BMPS (N-β-maleimidopropyl-oxysuccinimide ester), SM(PEG)12 (PEGylated, long-chain SMCC crosslinker), MBS (m-maleimidobenzoyl-N-hydroxysuccinimide ester), SMPB (succinimidyl 4-(p-maleimidophenyl)butyrate), succinimidyl 3-(2-pyridyldithio)propionate (SPDP), sulfo-LC-SPDP (sulfosuccinimidyl 6-(3'-(2-pyridyldithio)propionamido)hexanoate), sulfo-EMCS (N-ε-maleimidocaproyl-oxysulfosuccinimide ester), LC-SMCC (succinimidyl 4-(N-maleimidomethyl)cyclohexane-1-carboxy-(6-amidocaproate)), GMBS (N-γ-maleimidobutyryl-oxysuccinimide ester), SM(PEG)8 (PEGylated, long-chain SMCC crosslinker), sulfo-GMBS (N-γ-maleimidobutyryl-oxysulfosuccinimide ester), sulfo-SMPB (sulfosuccinimidyl 4-(N-maleimidophenyl)butyrate), sulfo-KMUS (N-κ-maleimidoundecanoyl-oxysulfosuccinimide ester), SMPH (succinimidyl 6-((beta-maleimidopropionamido)hexanoate)), SM(PEG)4 (PEGylated SMCC crosslinker), AMAS (N-α-maleimidoacet-oxysuccinimide ester), SMCC (succinimidyl 4-(N-maleimidomethyl)cyclohexane-1-carboxylate), sulfo-MBS (m-maleimidobenzoyl-N-hydroxysulfosuccinimide ester), PEG12-SPDP (PEGylated, long-chain SPDP crosslinker), SMCC (succinimidyl trans-4-(maleimidylmethyl)cyclohexane-1-carboxylate), LC-SPDP (succinimidyl 6-(3(2-pyridyldithio)propionamido)hexanoate), EMCS (N-ε-malemidocaproyl-oxysuccinimide ester), SBAP (succinimidyl 3-(bromoacetamido)propionate), SPDP (succinimidyl 3-(2-pyridyldithio)propionate), PEG4-SPDP (PEGylated, long-chain SPDP crosslinker), SIA (succinimidyl iodoacetate), SM(PEG)2 (PEGylated SMCC crosslinker), and SM(PEG)24 (PEGylated, long-chain SMCC crosslinker).

Other crosslinkers include sulfhydryl-to-sulfhydryl crosslinkers such as tris(2-maleimidoethyl)amine (TMEA), bismaleimidohexane (BMH), 1,11-bismaleimido-triethyleneglycol (BM(PEG)3), 1,4-bismaleimidobutane (BMB), 1,8-bismaleimido-diethyleneglycol (BM(PEG)2), bismaleimidoethane (BMOE), and dithiobismaleimidoethane (DTME). Further crosslinkers include sulfhydryl-to-carbohydrate crosslinkers such as 4-(4-N-maleimidophenyl)butyric acid hydrazide (MPBH), N-β-maleimidopropionic acid hydrazide (BMPH), N-κ-maleimidoundecanoic acid hydrazide (KMUH), 3-(2-pyridyldithio)propionyl hydrazide (PDPH), and N-ε-maleimidocaproic acid hydrazide (EMCH).

c. Fluorescent Dyes

Suitable fluorescent dyes that may be used to prepare PNPs are known in the art, and include but are not limited to fluoresceins, rhodamines, coumarins, pyrenes, cyanines, squaraines, and boron-dipyrromethenes. Fluorescent dye reagents will typically include the fluorescent dye along with one or more reactive moieties, such as N-succinimidyl esters or isothiocyanates, which react with an accessible side chain on a protein such as an amine (e.g., from a lysine side chain), carboxylic acid (e.g., from an aspartic acid or glutamic acid side chain) or a thiol (e.g., from a cysteine side chain). For example, fluorescent dye reagents that are commercially available include but are not limited to: 5- and 6-carboxyfluoresceins and esters thereof; fluorescein isothiocyanate (e.g., fluorescein-5-isothiocyanate or fluorescein-6-isothiocyanate); BODIPY® dyes commercially available from Molecular Probes; Alexa Fluor® dyes commercially available from Molecular Probes; CyDye fluors commercially available from GE Healthcare Biosciences; HiLyte™ Fluor Dyes available from AnaSpec; and VivoTag™ fluorophores available from PerkinElmer.

Particular fluorescent dye reagents that can be used in the disclosed methods include, but are not limited to: 1-pyrenebutanoic acid N-succinimidyl ester; 7-methoxycoumarin-3-carboxylic acid N-succinimidyl ester; 7-diethylaminocoumarin-3-carboxylic acid N-succinimidyl ester; fluorescein isothiocyanate; tetramethylrhodamine-5-(and-6)-isothiocyanate; coumarin 540A (also known as coumarin 153, having the formula 2,3,6,7-tetrahydro-9-(trifluoromethyl)-1H,5H, 11H-[1]benzopyrano(6,7,8-ij)quinolizin-11-one); and 5(6)-carboxy-X-rhodamine N-succinimidyl ester.

Those skilled in the art will appreciate that the protein fluorescent nanoparticles will include the fluorescent dye component of the fluorescent dye reagent, covalently bound to the protein, potentially via one or more linking atoms or groups.

The fluorescent dye can be chosen to impart specific properties to the nanoparticles, such as a particular color of fluorescence. In certain embodiments, multiple different fluorescent dyes can be used with single nanoparticles to produce white fluorescence. For example, in some embodiments, the method comprises labeling the protein with more than one fluorescent dye reagent. In some embodiments, the method comprises labeling the protein with at least three or four (or more) different fluorescent dye reagents. In some embodiments, the protein is labeled with three or four fluorescent dye reagents selected from 7-methoxycoumarin-3-carboxylic acid N-succinimidyl ester, 7-diethylaminocoumarin-3-carboxylic acid N-succinimidyl ester; fluorescein isothiocyanate, and 5(6)-carboxy-X-rhodamine N-succinimidyl ester. In some embodiments, the methods can use 7-methoxycoumarin-3-carboxylic acid N-succinimidyl ester, fluorescein isothiocyanate, and 5(6)-carboxy-X-rhodamine N-succinimidyl ester, which can produce PNPs that emit white fluorescence. In some embodiments, the methods can use 7-diethylaminocoumarin-3-carboxylic acid N-succinimidyl ester, fluorescein isothiocyanate, and 5(6)-carboxy-X-rhodamine-N-succinimidyl ester, which can produce PNPs that emit white fluorescence.

Following labeling with one or more fluorescent dyes, the PNPs can fluoresce when excited with light of an appropriate wavelength. Fluorescent properties of the PNPs are further described herein below.

d. Reaction Times

The steps of nanoparticle synthesis, including the crosslinking step and the labeling step, can be carried out for suitable time periods in order to form the fluorescent protein particles of a desired size and of a desired degree of labeling.

In embodiments in which the protein is labeled with a fluorescent dye reagent before being crosslinked to form nanoparticles, or wherein the protein is first crosslinked to form nanoparticles and subsequently labeled with a fluorescent dye, the protein or the protein nanoparticles may be reacted with one or more fluorescent dye reagents for about 10 minutes to about 4 hours or longer, e.g., about 10 minutes, about 20 minutes, about 30 minutes, about 40 minutes, about 50 minutes, about 60 minutes, about 1.1 hours, about 1.2 hours, about 1.3 hours, about 1.4 hours, about 1.5 hours, about 1.6 hours, about 1.7 hours, about 1.8 hours, about 1.9 hours, about 2 hours, about 2.1 hours, about 2.2 hours, about 2.3 hours, about 2.4 hours, about 2.5 hours, about 2.6 hours, about 2.7 hours, about 2.8 hours, about 2.9 hours, about 3 hours, about 3.1 hours, about 3.2 hours, about 3.3 hours, about 3.4 hours, about 3.5 hours, about 3.6 hours, about 3.7 hours, about 3.8 hours, about 3.9 hours, about 4 hours, or longer.

In embodiments in which the protein is labeled with a fluorescent dye reagent before being crosslinked to form nanoparticles, or wherein the protein is first crosslinked to form nanoparticles and subsequently labeled with a fluorescent dye, the protein or the labeled protein can be reacted with the crosslinking reagent for about 1 hour to about 24 hours, for example, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or more as needed to form nanoparticles of the desired size.

e. Metal Nanoclusters

In some embodiments, the methods involve formation of a metal nanocluster. Formation of the metal nanocluster can be further incorporated into the methods of preparing protein fluorescent nanoparticles that involve labeling with a fluorescent dye reagent and crosslinking the protein. For example, the methods can include a step of forming a metal nanocluster in the protein, either before or after the crosslinking step.

In another aspect, disclosed is a method for synthesizing protein fluorescent nanoparticles, the method comprising: providing a solution comprising a protein and a metal-containing reagent; forming a metal nanocluster from the metal-containing reagent; and adding a crosslinking agent to crosslink the protein, to thereby form the protein fluorescent nanoparticles. In another embodiment, the method comprises: crosslinking a protein with a crosslinking agent to form protein nanoparticles; and adding a metal-containing reagent to the protein nanoparticles, to thereby form the protein fluorescent nanoparticles. In some embodiments, the protein nanoparticles can be annealed prior to addition of the metal containing reagent (see below).

In suitable embodiments, the metal is gold. In some embodiments, the metal-containing reagent is $HAuCl_4$ (gold colloid, such as that available from Sigma-Aldrich).

Metal nanoclusters can be formed by addition of the metal-containing reagent, followed by heated to an appropriate temperature for a suitable period of time to allow nanoclusters to form. For example, following addition of a metal-containing reagent, the sample can be heated to a temperature of about 40° C. to about 50° C., e.g., about 41° C., about 42° C., about 43° C., about 44° C., about 45° C., about 46° C., about 47° C., about 48° C., about 49° C., or about 50° C., or a higher temperature as needed. The sample can be heated for a period of time of about 30 minutes to about 24 hours, e.g., about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

Particles prepared with gold nanoclusters can emit fluorescence when excited with UV light. When using the method in which the gold nanoclusters are prepared after the protein nanoparticles are formed, upon excitation at 360 nm, the emission peak is seen at 450 nm; this may be due to the proximity of gold nanoclusters within the binding pockets of BSA. Using the method in which the gold nanoclusters are prepared before the protein nanoparticles are formed, upon excitation at 360 nm, the emission peak is seen at 650.

f. Particle Size Control

In the methods of synthesizing PNPs, the particle size can be regulated by controlling the concentration of the fluorescent dye, the type of fluorescent dye, the pH of the reaction mixture, and the reaction temperature or time. Further details can be found in the Examples.

The methods described herein can produce PNPs having diameters or an average particle size of about 10 nm to about 100 nm. For example, the average particle size may be about 10 nm, about 15 nm, about 20 nm, about 25 nm, about 30 nm, about 35 nm, about 40 nm, about 45 nm, about 50 nm, about 55 nm, about 60 nm, about, 65 nm, about 70 nm, about 75 nm, about 80 nm, about 85 nm, about 90 nm, about 95 nm, or about 100 nm.

In some embodiments, the methods produce PNPs having a single average particle size of about 10 nm to about 100 nm, for example, about 10 nm, about 15 nm, about 20 nm, about 25 nm, about 30 nm, about 35 nm, about 40 nm, about 45 nm, about 50 nm, about 55 nm, about 60 nm, about, 65 nm, about 70 nm, about 75 nm, about 80 nm, about 85 nm, about 90 nm, about 95 nm, or about 100 nm.

In some embodiments, the methods produce PNPs having a bimodal distribution of particle sizes, with two distinct groups of particles having different average sizes. The two average particle sizes in the bimodal distribution may be selected from about 10 nm, about 15 nm, about 20 nm, about 25 nm, about 30 nm, about 35 nm, about 40 nm, about 45 nm, about 50 nm, about 55 nm, about 60 nm, about, 65 nm, about 70 nm, about 75 nm, about 80 nm, about 85 nm, about 90 nm, about 95 nm, or about 100 nm. For example, particles may have a bimodal distribution with one group of particles having an average particle size of about 10 nm, and another group of particles having an average particle size of about 50 nm.

In some embodiments, the methods can be carried out at a suitable pH to promote formation of particular particle sizes. For example, the pH can be selected based on the pI of the protein used to prepare the nanoparticles. In suitable embodiments, the synthetic method can be carried out at a pH of about 6.0 to about 9.0, for example, about 6.0, about 6.5, about 7.0, about 7.5, about 8.0, about 8.5 or about 9.0.

In some embodiments, the methods can include further steps to achieve particular particle sizes. For example, in some embodiments, the methods can include an annealing step. For example, the particles can be annealed at 80-90° C. (e.g., 85° C.) for a suitable period of time (e.g., 1-15 minutes, e.g., 5 minutes).

g. Further Modification

In the disclosed methods, the PNPs can be further modified to label the nanoparticles with different compounds, or to load the nanoparticles with various payload materials. For example, the nanoparticles can be prepared in the presence of a small molecule that can be embedded in the nanoparticles, such as drug molecules, signal peptides, cell-recognition elements or amino acids; these can potentially be used for cell uptake or drug delivery. The nanoparticles can also be labeled with additional molecules, such as biological compounds for targeting to various cells or tissues; for example, nanoparticles can be modified with taurine, which has been shown to promote cellular uptake. For example, taurine labeled particles can be internalized much more rapidly than unlabeled particles. In other embodiments, nanoparticles can be modified with biotin, which can facilitate their labeling and/or detection with streptavidin.

In some embodiments, the protein can be modified to attach a molecule, such as a biological compound (e.g., taurine or biotin) prior to crosslinking the protein to form nanoparticles. In some embodiments, the protein can be modified to attach a molecule, such as a biological compound (e.g., taurine or biotin) after the protein has been crosslinked to form nanoparticles.

3. PROTEIN FLUORESCENT NANOPARTICLES

Also disclosed herein are PNPs that are prepared via methods disclosed herein. The nanoparticles may have sizes disclosed herein, and properties disclosed herein.

In some embodiments, disclosed herein is a protein fluorescent nanoparticle, wherein the protein fluorescent nanoparticle comprises a protein that is labeled with a fluorescent dye, wherein the protein is cross-linked using a cross-linker, and wherein the nanoparticles have an average size of about 10 nm to about 100 nm. The protein, fluorescent dye and cross-linker are the same as those described in the section above regarding methods of synthesis.

a. Fluorescent Properties

The PNPs disclosed herein, including PNPs prepared by methods disclosed herein, exhibit fluorescence when exposed to light of a suitable excitation wavelength. For example, if a PNP is prepared with a particular fluorescent dye, the PNP will exhibit fluorescence at a particular emission wavelength when excited at the corresponding excitation wavelength for that fluorescent dye. For example, suitable excitation and emission wavelengths for certain fluorescent dyes that are incorporated in to the PNPs described herein are as follows:

1-pyrenebutanoic acid N-succinimidyl ester: $\lambda_{ex}$=340 nm, $\lambda_{em}$=376 nm;
7-methoxycoumarin-3-carboxylic acid N-succinimidyl ester: $\lambda_{ex}$=358 nm, $\lambda_{em}$=410 nm;
7-diethylaminocoumarin-3-carboxylic acid N-succinimidyl ester: $\lambda_{ex}$=445 nm, $\lambda_{em}$=482 nm;
fluorescein isothiocyanate: $\lambda_{ex}$=494 nm, $\lambda_{em}$=519 nm;
tetramethylrhodamine-5-(and-6)-isothiocyanate: $\lambda_{ex}$=543 nm, $\lambda_{em}$=571 nm; and
5(6)-carboxy-X-rhodamine N-succinimidyl ester: $\lambda_{ex}$=576 nm, $\lambda_{em}$=601 nm.

Those skilled in the art will appreciate that excitation and emission maxima for particular fluorescent dyes are approximate and may vary slightly depending on the environment of the dye following conjugation. Exact peak excitation and emission wavelengths may vary slightly from those listed above, once the fluorescent dye is incorporated in to the PNPs. The term "about" as used herein to refer to excitation or emission wavelengths is intended to indicate that the peak excitation or emission wavelength may vary, for example, by 5-10 nm on either side of the peak.

In some embodiments, the nanoparticle may have a peak emission wavelength at about 375 nm, about 400 nm, about 472 nm, about 520 nm, about 571 nm, about 601 nm, or about 710 nm. In some embodiments, the nanoparticle may have four or five peak emission wavelengths selected from the group consisting of about 345 nm, about 400 nm, about 520 nm, about 601 nm, and about 710 nm.

For PNPs exhibiting white fluorescence, e.g., PNPs labeled with more than one fluorescent dye such as those labeled with three or four fluorescent dyes, the PNPs may be excited at suitable wavelengths. Certain PNPs exhibiting white fluorescence can be excited at 254 nm (e.g., using a mercury lamp). Certain other PNPs exhibiting white fluorescence can be excited at 405 nm (e.g., using an appropriate laser diode).

When PNPs are prepared using gold nanoclusters, the PNPs may emit fluorescence at 450 nm or 650 nm as well as long-lived phosphorescence at 710 nm.

b. Chromaticity Coordinates

The PNPs disclosed herein, including PNPs prepared by methods disclosed herein, may have certain chromaticity coordinates. Generally, chromaticity is an objective specification of the quality of a color. One particular expression of chromaticity uses the 1931 CIE (x,y) chromaticity coordinates, created by the Commission Internationale d'Eclairage (International Commission on Illumination, or CIE) in 1931. As those skilled in the art will appreciate, pure white light has chromaticity coordinates of (x=0.33, y=0.33) (abbreviated as (0.33, 0.33)).

The PNPs disclosed herein that exhibit white fluorescence may have chromaticity coordinates in which x is about 0.30 to about 0.40, for example about 0.30, about 0.31, about 0.32, about 0.33, about 0.34, about 0.35, about 0.36, about 0.37, about 0.38, about 0.39 or about 0.40. The PNPs disclosed herein that exhibit white fluorescence may have chromaticity coordinates in which y is about 0.30 to about 0.40, for example about 0.30, about 0.31, about 0.32, about 0.33, about 0.34, about 0.35, about 0.36, about 0.37, about 0.38, about 0.39 or about 0.40. For example, the chromaticity coordinates of a white PNP disclosed herein may be (0.30, 0.36).

c. Quantum Yield

The PNPs disclosed herein, including PNPs prepared by methods disclosed herein, may have certain quantum yields. The quantum yield ($\Phi$) is the ratio of photons absorbed to photons emitted through fluorescence. In other words, quantum yield is the emission efficiency of a given fluorophore, and provides the probability that an excited state is deactivated by fluorescence rather than by another non-radiative mechanism.

The PNPs disclosed herein may have quantum yields of about 0.2 to about 50. For example, the PNPs disclosed herein may have quantum yields of about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50.

4. METHODS OF USE

The PNPs can be used in a variety of applications, including those applications for which traditional quantum dots are used. Exemplary applications include cellular imaging, protein delivery, drug delivery, pH sensing, temperature sensing, and other applications.

a. Cellular Imaging

Provided herein is a method of imaging a cell, comprising: contacting the cell with a protein fluorescent nanoparticle disclosed herein, such as a protein fluorescent nanoparticle prepared according to a method disclosed herein; and detecting the protein fluorescent nanoparticle in the cell (e.g., using fluorescence imaging).

Currently, organic dyes and carbon quantum dots are being used to image cells and study cellular mechanisms. The PNPs disclosed herein can perform the same function with the added bonus of being mainly composed of biological components, biocompatible, and multiple wavelengths can be monitored simultaneously for ratiometric measurements which are much more robust than single wavelength measurements.

As disclosed in the Examples herein, certain PNPs can enter cells (e.g., PNPs based on glucose oxidase), allowing them to be used for cellular imaging. The methods can be used in a variety of cell lines, including cancer cell lines (e.g., HN12 oral cancer cells, A549 adenocarcinomic human alveolar basal epithelial cells, HeLa human cervical cancer cells, MDAMB231 human breast cancer cells, PC3-20 human prostate cancers, L6 rat myoblast cells, and OVCAR-8 human ovarian cancer cells).

b. Protein Delivery/Transfection

The disclosed protein nanoparticles are used for the uptake of specific proteins into the cell, and hence, the cellular biochemical pathways can be manipulated using protein nanoparticles. This can be an alternative to the use of DNA or RNA for the control of cellular biochemical pathways.

c. pH Sensing

The disclosed PNPs can be used for pH sensing applications. Provided herein is a method of detecting pH in a sample, comprising: contacting the cell with a white-emitting protein fluorescent nanoparticle disclosed herein, such as a white-emitting protein fluorescent nanoparticle prepared according to a method disclosed herein; and detecting emission from the white-emitting protein fluorescent nanoparticle in the sample over a range of pH values from about 2 to about 11.

For example, nanoparticles disclosed herein, particularly those labeled with multiple fluorescent dyes that produce white light emission have fluorescent properties that change depending on pH over a broad range of pH 2-11. Particles may have white fluorescence emission at pH 7, which may change when the pH is lowered or raised. Since white light purity depends on a combination of red green and blue components of the emitted light, a small change in any of these component intensities will produce off-white emission, which is readily detectable by the naked eye. The particles may therefore be used to sense pH in various biological imaging applications.

The influence of pH on the emission is reversible, thus the pH sensing can be conducted over various cycles of changes in pH.

d. Temperature Sensing

The disclosed PNPs can also be used for temperature sensing applications. The disclosed PNPs can be used for pH sensing applications. Provided herein is a method of detecting pH in a sample, comprising: contacting the cell with a white-emitting protein fluorescent nanoparticle disclosed herein, such as a white-emitting protein fluorescent nanoparticle prepared according to a method disclosed herein; and detecting emission from the white-emitting protein fluorescent nanoparticle in the sample over a range of temperatures from about 20° C. to about 80° C.

For example, PNPs labeled with three different fluorescent dyes can be used for temperature sensing by monitoring the ratiometric measurement of emission from two dyes, while a third dye can serve as a built-in internal standard.

e. Drug Delivery

The protein nanoparticles function also as drug delivery vehicles with or without further labeling. A number of different organic molecules can be embedded within these nanoparticles for drug delivery.

f. Other Uses

Other uses for the disclosed nanoparticles include protein transduction, multi-colored imaging and biological LEDs, solar light gathering and conversion.

5. EMBODIMENTS

Certain non-limiting embodiments of the disclosure are as follows.

1. A method of synthesis for fluorescent dye-labeled protein nanoparticles in which nanoparticles are formed from proteins such as BSA via crosslinking with 1-ethyl-3-(-3-dimethylaminopropyl) carbodiimide (EDC), wherein the crosslinking takes place either before or after linking the dyes to the protein.

2. A method of synthesis for fluorescent dye-labeled protein nanoparticles in which nanoparticles are formed from proteins such as BSA, wherein the method is described in the Examples section.

3. A fluorescent dye-labeled protein nanoparticle, wherein the size of the nanoparticle can be controlled/tuned.

4. The fluorescent dye-labeled protein nanoparticle of embodiment 3, wherein the size of the nanoparticle is about 10 nm to about 50 nm.

5. A fluorescent dye-labeled protein nanoparticle, wherein the color of the nanoparticle can be controlled/tuned.

6. The fluorescent dye-labeled protein nanoparticle embodiment 5, wherein the color of the nanoparticle is selected from red, green, blue and yellow, depending on the dye or combination of dyes used.

7. The fluorescent dye-labeled protein nanoparticle of embodiment 5, wherein the peak emission wavelength of the nanoparticle is about 375, 400, 520, 571, or 601 nm.

8. The fluorescent dye-labeled protein nanoparticle of embodiment 5, wherein the fluorescent label is selected from: 1-pyrenebutanoic acid N-succinimidyl ester (P); 7-methoxycoumarin-3-carboxylic acid N-succinimidyl ester (M); 7-diethylaminocoumarin-3-carboxylic acid N-succinimidyl ester (D); fluorescein isothiocyanate (F); tetramethylrhodamine-5-(and-6)-isothiocyanate (T); and 5(6)-carboxy-X-rhodamine N-succinimidyl ester (R).

9. The fluorescent dye-labeled protein nanoparticle of embodiment 5, wherein the color of the nanoparticle is white, predominantly white or a nearly white color.

10. The fluorescent dye-labeled protein nanoparticle of embodiment 9, wherein the fluorescent label comprises a combination of three or more dyes attached to the same nanoparticle such that the overall emission is white, predominantly white or a nearly white color.

11. The fluorescent dye-labeled protein nanoparticle of embodiment 9, wherein the fluorescent label comprises 7-methoxycoumarin-3-carboxylic acid N-succinimidyl ester (M), fluorescein isothiocyanate (F), or 5(6)-carboxy-X-rhodamine N-succinimidyl ester (R), or a mixture of any thereof.

12. The fluorescent dye-labeled protein nanoparticle of embodiment 9, wherein the nanoparticle had four emission peak wavelengths of about 345, 400, 520 and 601 nm.

13. A mixture of the fluorescent dye-labeled protein nanoparticles of embodiments 5 to 8, wherein the overall emission of the mixture is white, predominantly white or a nearly white color.

6. EXAMPLES

Example 1. Synthesis and Characterization of Exemplary Nanoparticles

In this example, the following abbreviations are used: CD is circular dichroism; TEM is transmission electron microscopy; DLS is dynamic light scattering; PNPA is para-nitrophenyl acetate; SDS-PAGE is sodium dodecyl sulfate polyacrylamide gel electrophoresis.

Proteins and Chemicals.

All reagents were purchased from commercial sources and used as received unless otherwise indicated. For example, glucose oxidase (GO, *Aspergillus niger*), horseradish peroxidase (HRP, *Amoracia rusticana*), lipase (*Candida rugosa*), sodium phosphate ($Na_2HPO_4$), fluorescein isothiocyanate (FITC), 1-ethyl-3-(-3-dimethylaminopropyl) carbodiimide (EDC), pyrene-3-butyric acid (PBA), and coumarin 540A (C540A, also known as coumarin 153 and having the formula 2,3,6,7-tetrahydro-9-(trifluoromethyl)-1H,5H,11H-[1]benzopyrano(6,7,8-ij)quinolizin-11-one) were purchased from Sigma (St. Louis, Mo.). Bovine serum albumin (BSA) and catalase were purchased from US Biologicals (Salem, Mass.) and Worthington Biochemical Co., (Lakewood, N.J.), respectively.

Synthesis of Nanoparticles using FITC.

Protein solutions were prepared by stirring protein (3 mg/mL) in 0.1 M carbonate/bicarbonate buffer, pH adjusted to 9.0. A solution of FITC (0.075 mg/mL, 0.2 mM) in DMSO was added to the protein solution and stirred for 1.3 h. The pH of the resulting solutions was adjusted depending on the pI of the protein (see Table 1 below). Finally, a solution of EDC (10 mg/mL, 52 mM) was added to the protein/fluorescein solution and stirred overnight. The nBSA particle size increased with reaction time (see FIG. 4) and particle size has been conveniently controlled a by adjusting the reaction time. Samples were dialyzed (25 kDa cutoff membranes, 10 mM $Na_2HPO_4$ pH 6.0) or purified by ultrafiltration until the filtrates were free of FITC. Samples were routinely analyzed by agarose gel electrophoresis and SDS-PAGE (see below) for purity.

TABLE 1

| Conditions Used for Synthesis of Nanoparticles | | |
|---|---|---|
| Protein | Protein pI | Synthesis pH |
| GO | 4.2 | 6 |
| BSA | 4.7 | 6 |
| HRP | 7.2 | 8 |
| Lipase | 4.9 | 9 |
| Catalase | 5.4 | 9 |

Dynamic Light Scattering (DLS) and Zeta Potential Studies.

Hydrodynamic radii were measured by means of photon correlation spectroscopy with Precision Detectors (Varian Inc.), CoolBatch+ dynamic light scattering apparatus with a 5×5 $mm^2$ square cuvette, 658 nm excitation laser source with a 90° geometry. Data collection was done at 26° C., for 1 s, 5 repetitions, with 60 accumulations after equilibrating the sample for 300 s. PNPs and their corresponding proteins (0.2 mg/mL in 10 mM $Na_2HPO_4$, pH 7) were routinely filtered with a 0.2 μm filter (PVDF, 13 mm, Fisher). Precision Elucidate v 1.1.0.9 and Precision Deconvolve v 5.5 were used to collect and process the data, respectively. Zeta potentials were measured on a Brookhaven Instruments Zeta Plus analyzer using the software from the manufacturer, as described before (Pattammattel et al. *Langmuir* 2013, 29, 2971-2981).

Transmission Electron Microscopy (TEM).

The nanoparticle solution (0.2 mg/mL) was applied to a carbon-coated Cu grid (400-mesh) after treating the grid with a plasma cleaner (Harrick PDC-32G). Aliquots of 3 μL were incubated on the grid for 60 s, blotted with filter paper (Whatman #4), and stained with 3 μL of 1% uranyl acetate for 30 s followed by blotting. After an hour of drying, the grids were imaged using a FEI Tecnai Spirit TEM with an operating voltage of 80 kV and a digital camera.

Spectral Measurements.

Absorption spectra were run on HP 8450 diode array spectrophotometer (Varian Inc., Santa Clara, Calif.) and fluorescence spectra were recorded on a homebuilt instrument interfaced with a Macintosh Mini operated by in-house software. To keep the absorbance less than 1, a short path length cuvette (1 mm×10 mm) was used, samples were excited at 495 nm, and all spectra were normalized to the same intensity for comparison.

Fluorescence Quenching Studies.

PNPs (prepared with catalase) were titrated with increasing concentrations of potassium iodide (KI) and FITC emission at 525 nm (exciting at 490 nm) monitored. Stern-Volmer plots were constructed and the quenching constants ($K_{sv}$) determined using the equation below, where $I_0$ is the fluorescence in the absence of the quencher and I the intensity in the presence of the quencher at concentration [Q].

$$I_0/I=1+K_{SV}[Q]$$

Activity Studies and Half-Lives of Nanoparticles at 60° C.

Enzymatic activities of PNPs and the unmodified enzymes were determined by reported methods (see below under the heading "Enzyme activity studies"), and specific activities determined from the initial rates (Nelson et al. *Anal. Biochem.* 1974, 59, 46-53; Anderson et al. *J. Chem. Educ.* 1994, 71, 715; Lee et al. *Angew. Chem. Int. Ed.* 2005, 117, 7593-7598). Time taken to reduce the enzymatic activity by half of its original activity (half-life) was estimated by measuring their activities at room temperature after heating at 60° C. for increasing lengths of time. Half-life was obtained by plotting specific activities of samples measured at room temperature, as a function of incubation time at 60° C.

Cellular Imaging Studies.

HN12 oral cancer cells were grown onto glass bottom microwell plates (#1.5 glass, MatTek Corporation), washed using DMEM without Phenol Red and FBS (Invitrogen) and incubated in the same media with 0.3 mg/mL of PNPs (see below under the heading "Internalization of nGO and Dextran-red by cells"). In some studies, A549 cells were used instead (see below under the heading "Imaging of A549 cells for the uptake of nBSA"). Live cell imaging was done at 37° C. in 5% $CO_2$ atmosphere (HN12 cells) using an inverted Zeiss LSM 700 confocal microscope, with Zen software 2010 (Carl Zeiss). For measuring the uptake and release kinetic measurements, a region of interest (ROI) was drawn around each cell and the average fluorescence intensity recorded in particular channels as a function of time.

Differential Scanning Calorimetry.

Thermal denaturation of PNPs was performed using Nano II differential scanning calorimeter (DSC) (model 6100, CSC, Utah). Unmodified protein and PNPs solutions (10 mM $Na_2HPO_4$ buffer pH 7.2) were scanned. The specific heat of the sample was measured as a function of temperature with respect to a reference cell, from 20 to 100° C., at a scan rate of 2° C./min. Excess molar heat capacities were calculated using molar masses of corresponding proteins. Model independent parameters such as peak transition temperature (Tm), the temperature where the denaturation begins, and $\Delta H_{denaturation}$ (integral CpdT) were extracted from the DSC data.

Synthesis and Size Control of nBSA PNPs.

Protein solution was prepared by stirring BSA (150 mg/mL) in d $H_2O$. Increasing amounts of EDC were added to the solution as it was stirred. The particle size was monitored via DLS. Once the desired particle size was reached, the particle formation reaction was quenched by adding 10 mM $HCO_3^-/CO_3^{-2}$ pH 9.0 buffer so that the final concentration of the protein was 75 mg/mL. To this diluted protein solution, 0.5% (w/w) FITC was added. The solution was allowed to stir in the dark for 2 h. The protein dot solution labeled with FITC was purified by filter centrifugation. Samples were spun at approximately 8000 rpm for 10 minutes until most of the protein solution had passed through the filter. Fresh DI $H_2O$ was added to the now concentrated solution in the centrifuge tube and spun again. This process was repeated until the solution passing through the filter was no longer yellow.

Agarose Gel Electrophoresis.

Agarose gels were prepared by dissolving agarose (0.5% w/v) (Sigma electrophoresis grade) in a hot solution of Tris acetate (40 mM, pH 6.5). The gel was placed on a horizontal gel electrophoresis apparatus (Gibco model 200, Life Technologies Inc, MD) and Tris acetate (40 mM pH 6.5) was used as the running buffer. Samples were loaded into the wells with loading buffer (50% v/v glycerol and 0.01% m/m bromophenol blue) and electrophoresis carried out for 30 minutes at 100 mV at room temperature. The gel was stained overnight with 10% v/v acetic acid, 0.02% m/m Coomassie Blue and then destained with 10% v/v acetic acid overnight.

SDS-PAGE.

A 7% separating with 5% stacking gel was used. Samples were prepared by adding loading buffer (10 μL, 2% SDS, 10% BME) to the sample and then boiled for 2 minutes. Samples were loaded into the gel so that each well contained 7.5 μg of protein in the well. The gel was run in Tris-glycine running buffer at 200 V constant in a Bio-Rad Mini Protean Electrophoresis apparatus until the dye front was approximately 1 cm from the bottom of the gel plate. The protein bands were visualized by Coomassie staining. Stain I (10% v/v acetic acid, 10% isopropanol, 0.02% Coomassie blue) was placed in the container with the gel and microwaved for 1 min. The solution was allowed to stand for 20 min. The gel was transferred to stain II (10% acetic acid, 0.02% Coomassie blue) and microwaved for 1 min before being allowed to stand for 20 min. Finally, the gel was transferred into destain (20% acetic acid), microwaved for 1 min, and allowed to stand for 20 min with a Kimwipe in the solution. The gels were photographed and processed with NIH Image J software.

Enzyme Activity Studies.

Activities of nGO were determined as reported (Nelson et al. *Anal. Biochem.* 1974, 59, 46-53). A solution of glucose (0.2 mM) was added to a mixture of nGO (1 μM), HRP (1 μM) in 10 mM $Na_2HPO_4$ buffer pH 7.2 and guaiacol (5 mM) dissolved in de-ionized distilled water. Oxidation of the substrate to the product, which has an absorption maximum at 470 nm, was monitored as a function of time (25° C.).

Activities of nLipase determined using p-nitrophenyl acetate (PNPA) as the substrate (Anderson et al., *J. Chem. Educ.* 1994, 71, 715). PNPA (20 μM in 5% acetonitrile) was added to the enzyme solution (1 μM) in 10 mM $Na_2HPO_4$ buffer pH 7.2 and absorbance at 410 nm recorded as a function of time. Initial rates and the specific activities were calculated using kinetic traces within the initial linear region of the data (first 50 seconds).

Peroxidase activities of nHRP and HRP were determined by a reported method with minor modifications (Lee et al. *Angew. Chem.* 2005, 117, 7593-7598). Guaiacol (2.5 mM) and $H_2O_2$ (0.5 mM) were added to enzyme solution (100 nM) in 10 mM $Na_2HPO_4$ buffer pH 7.2 and the product formation was monitored at 470 nm as a function of time. The kinetic data were used to extract initial rates and specific activities as described above.

Activities of nCatalase and catalase were measured by following the decomposition of $H_2O_2$ (20 mM). Hydrogen peroxide was added to the enzyme solution (1 μM) in 10 mM $Na_2HPO_4$ buffer pH 7.2. Decomposition of $H_2O_2$ was monitored by absorbance at 240 nm as a function of time.

Internalization of nGO and Dextran-Red by Cells.

HN12 cells were incubated with 0.5 mg/mL nGO-FITC (green) and 0.5 mg/ml Dextran Texas Red (MW 10000 Catalog #D1863, Invitrogen) for 2 h. Afterward cells were imaged for another 2.5 h to visualize internalization. Internalization of both dextran and nGO seems to occur both at the same time and is accompanied by significant blebbing of the plasma membrane, both of which indicates transient permeabilization of the membrane. The fluorescence of individual cells was quantified and shown in the graph (AU: arbitrary units), because different cells have different times and levels of internalization the graph of averaging all of them can become unclear.

Imaging of A549 Cells for the Uptake of nBSA.

A collection of $4\times10^4$ A549 cells/well were plated in an 8-well chamber and incubated at 37° C., 5% $CO_2$ for 4 h. DMEM cell Culture media containing 10% Fetal bovine serum, 1% Penicillin—streptomycin and 1% glutamine was removed and replaced with 200 μL of a dilution of Orange cell tracker CMTMR (Life technologies, Catalog number: C2927) (24 μM). Cells were incubated for 30 min at 37° C., 5% CO2, washed twice with PBS to remove the excess of cell tracker and new culture media was added. After incubating over night at 37° C., 5% CO2, the media was removed, cells were washed once with PBS and 200 μL of FITC, FITC+nGO, nBSA, nBSA+nGO dilutions in media without supplements were added at a concentration of 0.3 mg/mL. Cells were incubated for 4 h at 37° C., 5% $CO_2$. Confocal laser scanning microscopy (CLSM) was employed to investigate the presence of nanoparticles inside the cells.

nGO and Alexa555-Transferrin Release by Oral Cancer Cells after Uptake.

HN12 cells were incubated with 0.3 mg/ml nGO-FITC (green) and 20 μg/ml alexa555-Transferrin (red) for 3 h at 37° C., then cells were washed and imaged for 1 h to visualize their release.

Results and Discussion.

Figure 6:
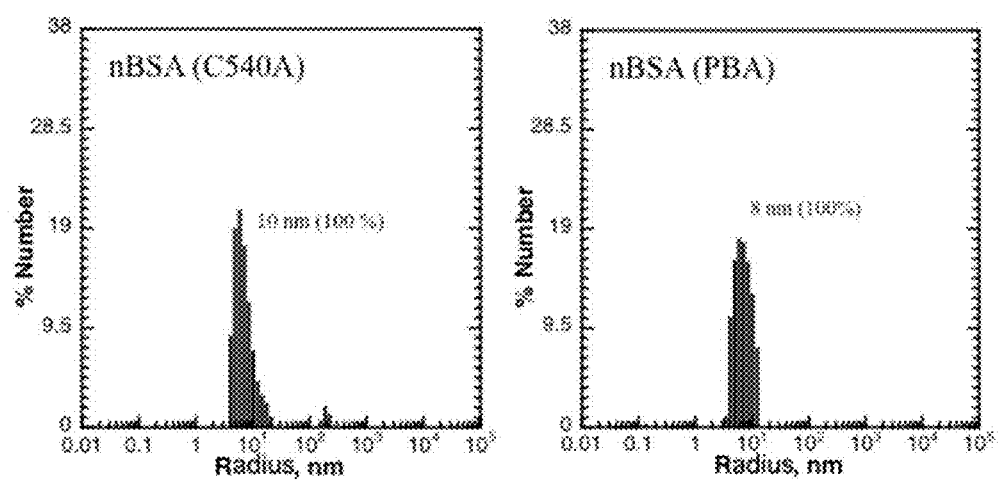
FIG. 6 shows DLS profiles of nanoparticles of BSA synthesized in the presence of two different dyes.

Synthesis of Protein Nanoparticles. In one approach (FIG. 1), the amino groups of the lysine residues of proteins are coupled with FITC, followed by controlled aggregation of proteins and then crosslinking the protein units by EDC (Table 1). FITC labeling of proteins is known to induce clustering, and here, these clusters were crosslinked to form stable particles. Nanoparticle formation was monitored by dynamic light scattering (DLS), gel electrophoresis, and TEM, and the reaction conditions have been optimized to consume all the free protein while producing the desired particle size. The resulting nanoparticles were purified by dialysis or by centrifugation/filtration, and they have been thoroughly characterized by physical/biochemical methods before cellular imaging. Particle size was regulated by controlling the concentration of the dye, type of the dye, pH, and reaction time. For example, nBSA size varied from 8 to 50 nm, depending on the type of dye used (FIG. 6).

Figure 3:
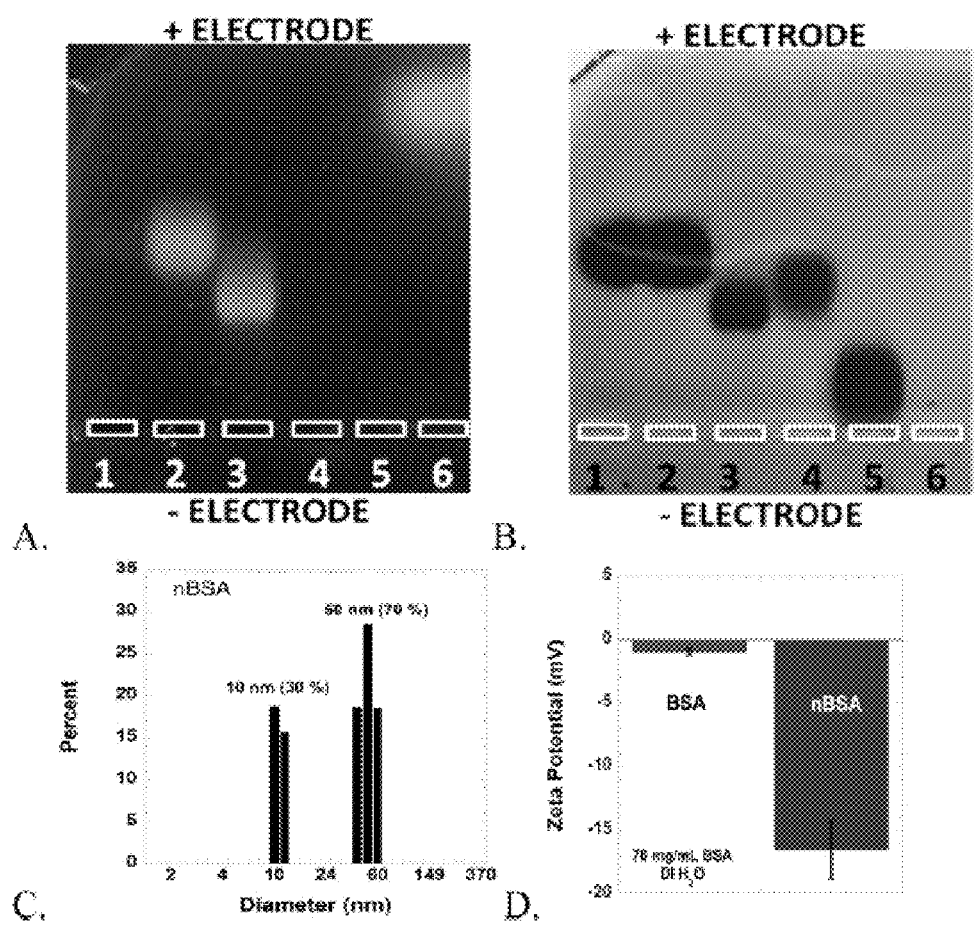
FIG. 3 shows: (A) an agarose gel (0.5%) under UV excitation of BSA (lane 1), BSA-FITC (lane 2), nBSA-FITC (lane 3), nGO (lane 5) and FITC (lane 6), where the bands are visible by their bright green fluorescence; (B) a standard photograph of the same agarose gel in (A) with Coomassie staining to reveal protein bands in blue; (C) a DLS plot of nBSA particles with diameters of 10 nm (30%) and 50 nm (70%); and (D) a zeta potential plot of BSA and nBSA.
Figure 4:
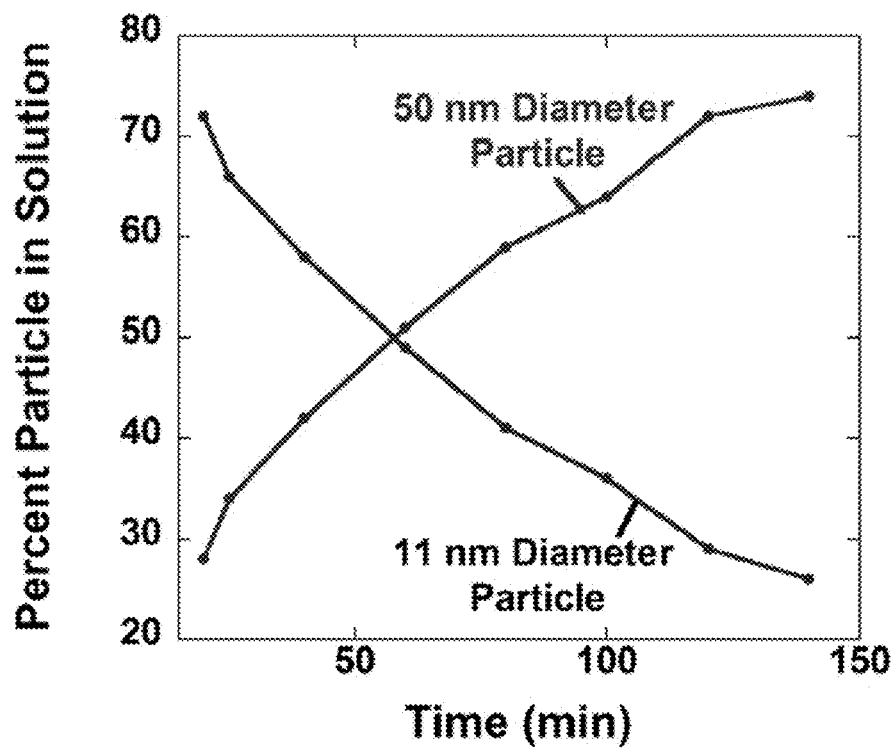
FIG. 4 shows a graph of the percent of certain PNPs in solution versus reaction time with a crosslinking agent, showing the increasing size of the particles as a function of reaction time.

Gel Electrophoresis. Agarose gel of nBSA obtained after 2 h of reaction time was imaged using UV excitation where the free FITC can be readily detected (FIG. 3A, lane 6) and the nBSA-FITC band (lane 3) is distinctly visible. The free BSA (lane 1) migrated much farther. Also, there was no free FITC in the nBSA-FITC lane. The same gel was also Coomassie stained to reveal the corresponding protein bands (FIG. 3B), and nBSA-FITC (lane 3) did not indicate any free BSA (lane 2). Thus, nBSA has no detectable amounts of either FITC or BSA, which is also confirmed by other methods described below. The formation of nBSA was also confirmed by DLS (FIG. 3C) where the nBSA indicated a major particle diameter of 50 nm (70%) and a minor fraction of 10 nm (30%) particles, but no free BSA. This was also confirmed by the fact that the population of the 50 nm particle increased while that of the 10 nm particle decreased simultaneously as a function of reaction time (FIG. 4). Thus, larger particles are produced from smaller ones as a function of reaction time, and this large particle size of nBSA (50 nm) explains its decreased mobility in the agarose gel (FIGS. 3A and 3B, lane 3).

Figure 5:
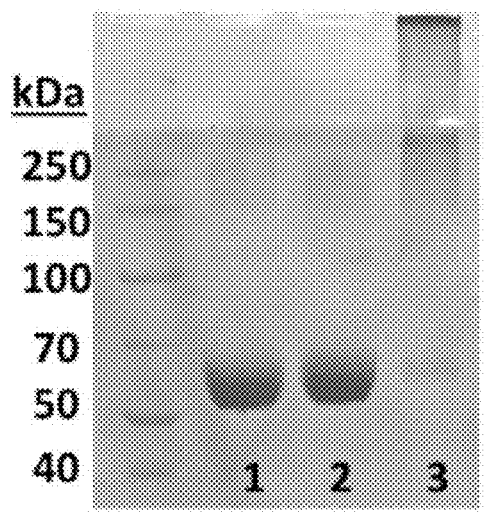
FIG. 5 shows an SDS-PAGE gel of nBSA samples: lane 1 is BSA, lane 2 is BSA-FITC, and lane 3 is nBSA, with a molecular weight ladder in the left-most lane and molecular weights of the ladder listed to the left of the gel.

Zeta potential studies of nBSA-FITC show a net negative charge of $-18\pm2$ mV (FIG. 3D), which is consistent with the consumption of the primary amine groups of BSA ($-1.0\pm0.2$ mV, DI) after reaction with FITC. On the other hand, EDC crosslinking consumes equal numbers of amine and carboxyl groups and this reaction should not change the net charge. When taken together, nBSA particles are expected to have increased negative charge when compared to BSA, and this has been verified by zeta potential studies. Despite this increased negative charge, the larger size of nBSA impeded its mobility in the agarose gel. The sample was also examined by SDS PAGE (FIG. 5), which indicated extensive crosslinking of BSA and resulted in higher-order aggregates and only a trace amount of BSA. Thus, the agarose gel, SDS PAGE, DLS, and zeta potential data confirm the formation and purity of nBSA.

Using the above EDC crosslinking method, nGO were also prepared (FIGS. 3A and 3B, lane 5), which moved far less than GO (lane 4). In contrast to the bimodal distribution of nBSA size, nGO indicated a single particle size of ~15 nm (100%). Similarly, nanoparticles were also made from HRP, lipase, and catalase, which consistently indicated reduced mobilities in agarose gels when compared to the respective unmodified proteins (data not shown). The isoelectric points of GO, BSA, and catalase are 4.2, 4.7, and 5.4, respectively. Therefore, they are all negatively charged at pH 7.0 (gel running buffer) and migrated toward the positive electrode. The corresponding nanoparticles were also negatively charged and migrated toward the positive electrode, but consistently to a lesser extent than their corresponding parents. The average pore size of the agarose gel (0.5% agarose) used here is ~450 nm and all nanoparticles readily migrated through these pores. The reaction conditions were optimized to produce nanoparticles without any leftover free protein.

To further test the generality of the above approach with other dyes, Coumarin 540A (C540A) and pyrene-3-butyric acid (PBA) were used in place of FITC to synthesize nBSA nanoparticles. The DLS (FIG. 6) indicated the corresponding radii to be 10 nm for nBSA-0540A (100%) and 8 nm for nBSA-PBA (100%). Thus, the dye-mediated aggregation followed by EDC crosslinking of the proteins produced different particle sizes depending on the dye used as well as the reaction time. This general, simple, versatile approach of making PNPs using a variety of dyes and proteins has significant advantages over reported methods. It produced much smaller fluorescent nanoparticles whose size can be tuned systematically while carrying different fluorophores.

Figure 7:
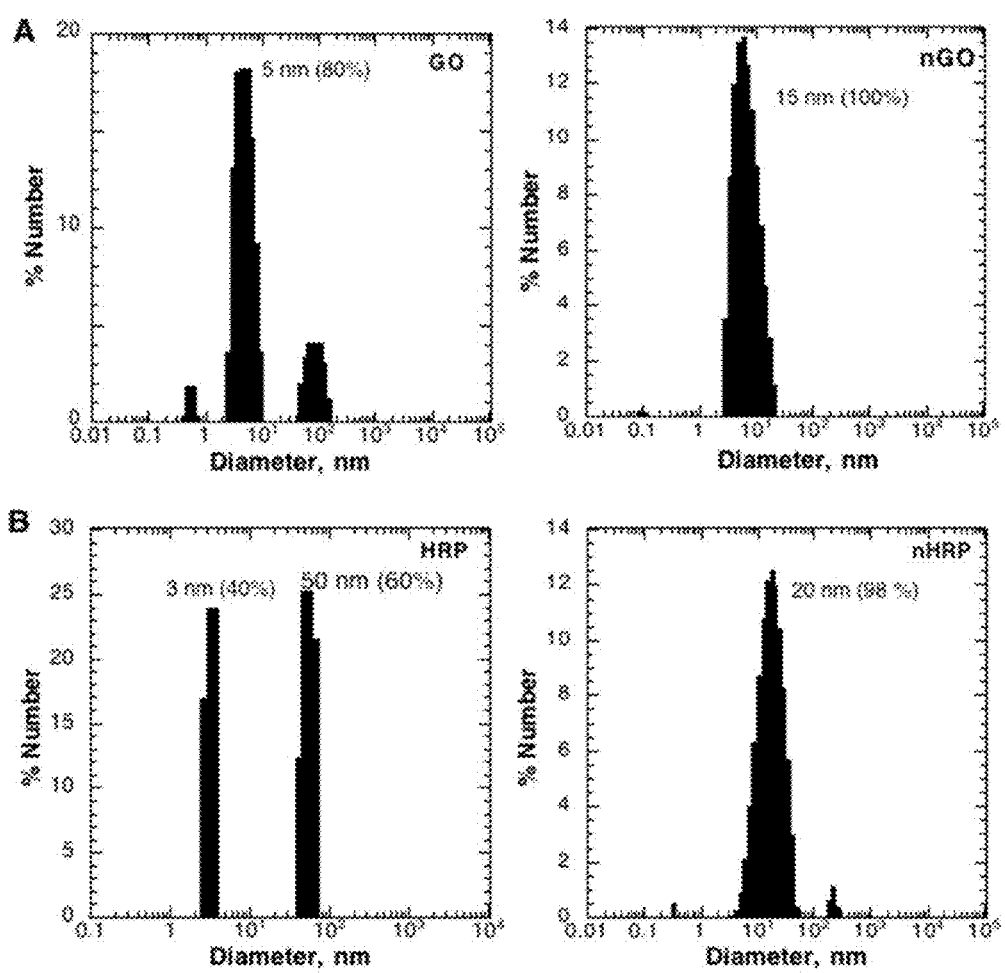
FIG. 7 shows DLS profiles of proteins (left panels) with corresponding nanoparticles (right panels) for: (A) GO and nGO; (B) HRP and nHRP; (C) Lipase and nLipase; and (D) Catalase and nCatalase.
Figure 7:
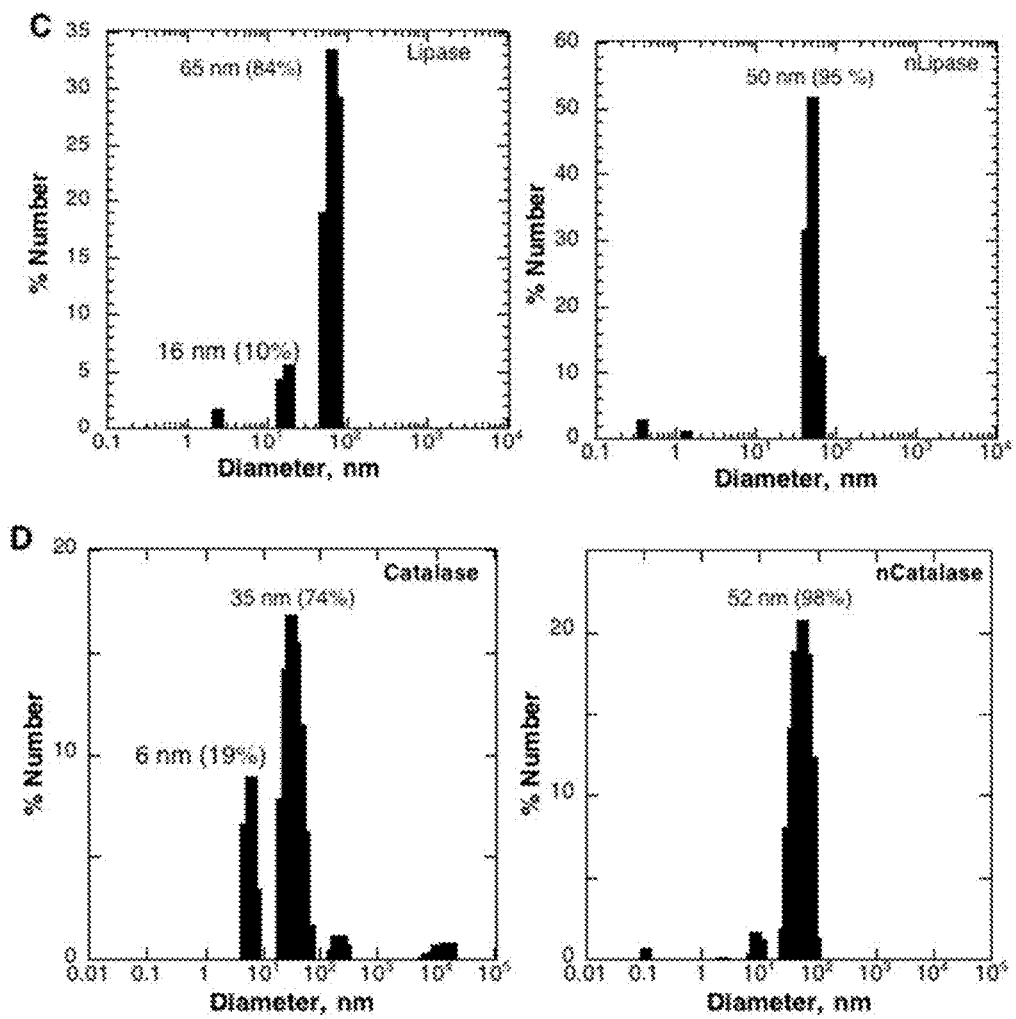

Sizes and Shapes of Nanoparticles. Dynamic light scattering (DLS) and transmission electron microscopy (TEM) were used to examine the morphology, sizes, and shapes of the nanoparticles. The hydrodynamic radii of nGO, nHRP, nLipase, and nCatalase were 8 (100%), 10 (98%), 25 (95%), and 25 (98%) nm, respectively (FIG. 7). In contrast, enzyme particles prepared by various precipitation methods produced 5-50 μm particles, which are unsuitable for a number of biological applications.

Figure 8:
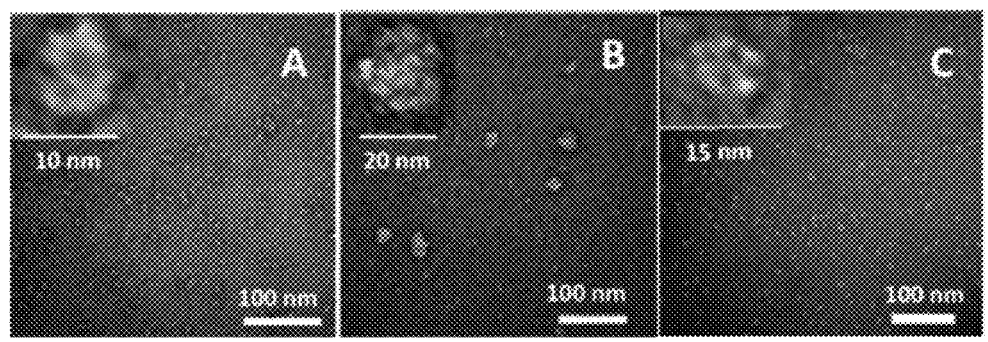
FIG. 8 shows TEM images of the following PNPs: (A) nGO; (B) nHRP; and (C) nLipase, all with uranyl acetate staining, where the bottom size bar represents 100 nm in all panels, and the inset shows the expanded view of one particle in each panel.

The DLS data are supported by the TEM micrographs (FIG. 8). Inset in each panel shows the expanded view of a single particle to clearly depict size and shape. Panel A shows nGO particles of size ~10 nm, whereas nHRP (panel B) had a diameter of ~20 nm and nLipase (panel C) a diameter of ~15 nm. These sizes are smaller than those noted in DLS, where the latter measures the hydrodynamic radius, which can be larger than the particle diameter. Drying of the samples on the TEM grid dehydrates the nanoparticles and shrinks them.

Figure 9:
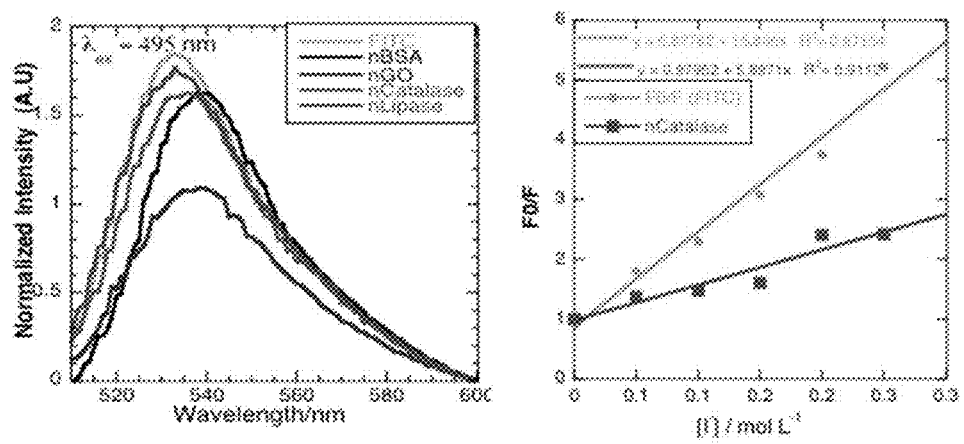
FIG. 9 shows: (A) Emission spectra of PNPs when compared to that of FITC (neon green). All spectra are normalized by dividing the intensities with their corresponding absorbances at 495 nm; (B) KI quenching of FITC (light green) and nCatalase-FITC (dark green, excited at 490 nm) emission, analyzed by Stern-Volmer equation.

Spectral Measurements and Fluorescence Quenching Studies. Emission properties of the nanoparticles were evaluated by fluorescence spectroscopy. As shown in FIG. 9A, fluorescence intensity of FITC bound to the nanoparticles maintained more than 80% of FITC emission except in the case of nGO where the intensity decreased substantially. Emission spectra corresponded to that of FITC and changes observed in emission spectral shifts and intensities are presumably due to attachment of the fluorophore to the protein. This possibility was tested in fluorescence quenching studies with potassium iodide (KI). Iodide quenched FITC fluorescence with a Stern-Volmer constant ($K_{sv}$) of 16 $M^{-1}$, whereas the corresponding $K_{sv}$ value of nCatalase was significantly less (6 $M^{-1}$, FIG. 9B). The decrease in $K_{sv}$ indicates that the fluorophore in the nanoparticles is protected by the protein matrix, likely due to its burial within the nanoparticles. Therefore, the nanoparticles are attractive for imaging studies since the fluorophore is also protected to a significant extent from quenchers in the environment by the protein matrix.

Protein Secondary Structure and Activity. The native structure of protein is vital for the retention of its biological activity. Therefore, the circular dichroism (CD) spectra of the nanoparticles were compared with those of the corresponding free proteins to evaluate any distortions in the secondary structures during/after the formation of the particles.

The far-UV-CD spectra showed strong peaks at 192 nm and strong double minima at 209 and 222 nm (see Table 2). The nanoparticle spectra were nearly superimposable with those of the corresponding free proteins, which indicated a significant retention of native-like secondary structures of the proteins present in the nanoparticles.

TABLE 2

| Sample | 222 nm | (Protein NP/Protein)$_{222}$ | 208 nm | 222/208 nm |
|---|---|---|---|---|
| BSA | −65 | 1.0 | −71 | 0.92 |
| nBSA | −71 | 1.1 | −76 | 0.93 |
| GO | −36 | 1.0 | −46 | 0.78 |
| nGO | −44 | 1.2 | −54 | 1.20 |
| Catalase | −9.0 | 1.0 | −21.0 | 2.30 |
| nCatalase | −8.0 | 0.9 | −24.0 | 3.00 |

In addition to the CD signals arising from the protein structure, we also observed induced CD (ICD) spectra for some of the nanoparticles, in the wavelength region corresponding to the fluorophore absorption band. For example, nBSA-FITC showed an intense ICD band at 550 nm, which is due to the interaction of the fluorophore with the protein environment and its proximity to the asymmetric centers of the amino acid units of the protein.

The retention of protein secondary structure in nanoparticles suggested the possibility of retention of their biological activity. Enzymatic assays were performed and specific rates compared with those of the corresponding free enzymes, under similar conditions of pH, buffer, ionic strength, and temperature. For example, the catalytic activity of nGO was monitored by the oxidation of D-glucose to gluconic acid with ambient oxygen, and the production of hydrogen peroxide was measured by its reaction with guaiacol (substrate), catalyzed by HRP. Guaiacol oxidation resulted in a colored product whose formation was monitored by following its absorption at 470 nm as a function of time. Catalytic activity of nGO at 25° C. is close to that of GO. Extensive structure retention and facile diffusion of the substrate to the active site of the enzyme in the nanoparticles, therefore, are permitted even after the particle formation, which indicates that the active sites of enzymes in these particles are accessible for small molecules.

Specific activities of the nanoparticles with respect to the corresponding unmodified enzymes are compared in FIG. 3B, and nGO and nHRP retained significant activity while nLipase and nCatalase indicated a significant drop (Table 3). Note that the latter two formed much larger particles and larger particles would decrease the mass transfer to the active sites that are located in the interior of the particles. Thus, controlling particle size is critical in retaining significant activity. Next, we examined the stabilities of the particles for practical considerations, and lower conformational entropy of the protein within the confines of the nanoparticles may enhance the nanoparticle thermal stability.

TABLE 3

Specific Activities of nanoparticles and corresponding unmodified proteins

| Sample | Specific Activity (AU/μM/s) |
|---|---|
| GO | $(1.000 \pm 0.0005) \times 10^{-2}$ |
| nGO | $(0.8000 \pm 0.0005) \times 10^{-2}$ |
| HRP | $(1.92 \pm 0.12) \times 10^{-2}$ |
| nHRP | $(1.32 \pm 0.08) \times 10^{-2}$ |
| Catalase | $(8.70 \pm 0.06) \times 10^{-1}$ |
| nCatalase | $(4.60 \pm 0.05) \times 10^{-1}$ |
| Lipase | $(1.33 \pm 0.09) \times 10^{-3}$ |
| nLipase | $(0.54 \pm 0.02) \times 10^{-3}$ |

Thermal and Storage Stabilities of Nanoparticles. Sufficient thermal and storage stabilities are essential for a wide use of protein nanoparticles. This metric was assessed by differential scanning calorimetry (DSC). DSC can provide a direct measure of the denaturation temperature ($T_d$), enthalpy (ΔH), heat capacity, and entropy changes. Both ΔH and $T_d$ are obtained from DSC in a model independent manner, even when the denaturation is irreversible. Thermograms of the nanoparticles, therefore, were quantified and compared with those of the corresponding parent proteins (Table S4). For example, $T_d$ of nGO was 71° C., far greater than that of GO (64° C.), $T_d$ of nBSA (67° C.) was much greater than that of BSA (60° C.), but nHRP and nCatalase had $T_d$ values of 85 and 64° C., respectively, which are about the same as those of their parent proteins. Thus, some nanoparticles gained enhanced stability.

TABLE 4

Thermodynamic parameters (ΔH) and denaturation temperatures ($T_m$) for the thermal denaturation of nanoparticles and the corresponding parent proteins

| Sample | ΔH (kcal/mol) | Tm (° C.) |
| --- | --- | --- |
| GO | 157 ± 24.7 | 60.0 ± 0.4 |
| nGO | 165 ± 10.8 | 67.0 ± 0.5 |
| HRP | 242 ± 13.0 | 63.5 ± 0.3 |
| nHRP | 260.3 ± 0.6 | 70.7 ± 0.1 |
| Catalase | 43.3 ± 1.0 | 84.0 |
| nCatalase | 31.5 ± 0.5 | 85.3 ± 0.05 |
| Lipase | 358.4 ± 33.6 | 63.5 ± 0.7 |
| nLipase | 400.5 ± 2.12 | 64.0 |

Figure 10:
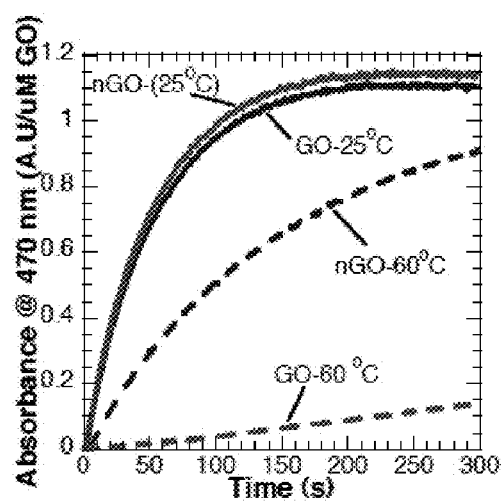
FIG. 10 shows kinetic traces showing nGO activity retention at 25° C. and several-fold enhanced activity of nGO after heating to 60° C. for 5 minutes and cooling to room temperature for 1 hour, when compared to that of GO subjected to the same conditions.

We further examined the thermal stability of nGO by heating to 60° C. for 5 min, followed by assessing their activities after cooling the samples to room temperature. nGO showed retention of 75% of its original activity after the heat treatment, while GO lost ~90% of its original activity under the same conditions (FIG. 10). Thus, nGO was more stable when challenged with heat, when compared to that of GO.

In addition to temperature stability, another challenge with proteins is their poor storage stability, which requires storage at low temperatures, which is not convenient. The nanoparticles are expected to have improved storage stabilities due to the encasement of proteins within the nanoparticles. To accelerate the nanoparticle aging, we chose to store them at 60° C., as a benchmark for stability ($Na_2HPO_4$ buffer pH 7.0), and examine activities. Aliquots of the samples were withdrawn, periodically, and specific activities measured at room temperature, and the time taken to decrease their original activity by 50% (storage half-life at 60° C.) has been calculated from plots of specific activities of the nanoparticles vs. storage time at 60° C.

Half-life of nGO increased to 30 min at 60° C., when compared to that of GO (7 min), and nLipase half-life improved to 130 min when compared to that of lipase (15 min), while the half-life of nHRP remained the same as that of HRP (400 min, 60° C.). Improved half-lives at 60° C. suggest that storage stabilities at room temperature could be even better, an important attribute for practical considerations.

Cellular Imaging Studies. The goal of producing stable, fluorescent, functional, biocompatible nanoparticles of controllable size has been aimed at testing their potential for cellular imaging. Cellular uptake and release studies with the nanoparticles were performed using HN12 or A549 cells which have been extensively used for imaging.

Incubation of HN12 cells with nBSA-FITC for extended periods of time (132 min) did not show any detectable uptake. A fluorescence micrograph recorded immediately after exposure of the HN12 cells to nBSA-FITC was essentially the same as the one recorded after 132 min of incubation, and the dark voids are the HN12 cells without the fluorophore; these matched well with the transmission micrographs. Thus, it can be concluded that nBSA-FITC is unable to enter the cells on these time scales. Similar negative results were obtained when the HN12 cells were exposed to nLipase, nHRP, and nCatalase (0.3 mg/mL, 132 min).

Figure 11:
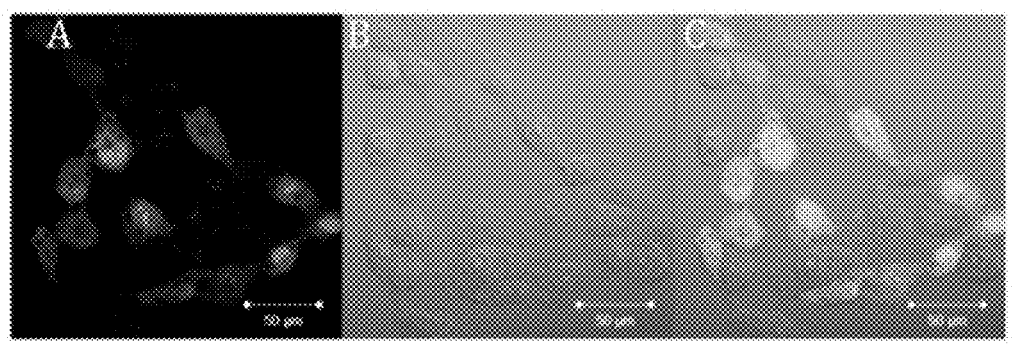
FIG. 11 shows: (A) a fluorescence micrograph after 4 hours; (B) a transmission micrograph after 4 hours; and (C) a superposition of the two, showing facile uptake of nGO-FITC by HN12 cells; the scale bar represents 50 µm.

In contrast to the lack of uptake of nBSA-FITC by HN12 cells, incubation with nGO-FITC (0.3 mg/mL protein) indicated rapid uptake, and uptake has been visualized after washing the cells to remove unabsorbed nGO-FITC from the media and then imaged (FIG. 11). Localization of this fluorescent signal within the cells is clearly seen with bright spots in certain areas (FIG. 11A, after 4 h). Superposition of the fluorescence (FIG. 11A) and transmission (FIG. 11B) images confirmed the uptake of nGO-FITC into the cells (FIG. 11C).

Some cells were without any fluorescence signal, which indicated a failure in the uptake of nGO-FITC. This phenomenon of uneven cellular uptake is not unusual for cancer cells, since they are not a homogeneous population and some are different from the others.

Figure 12:
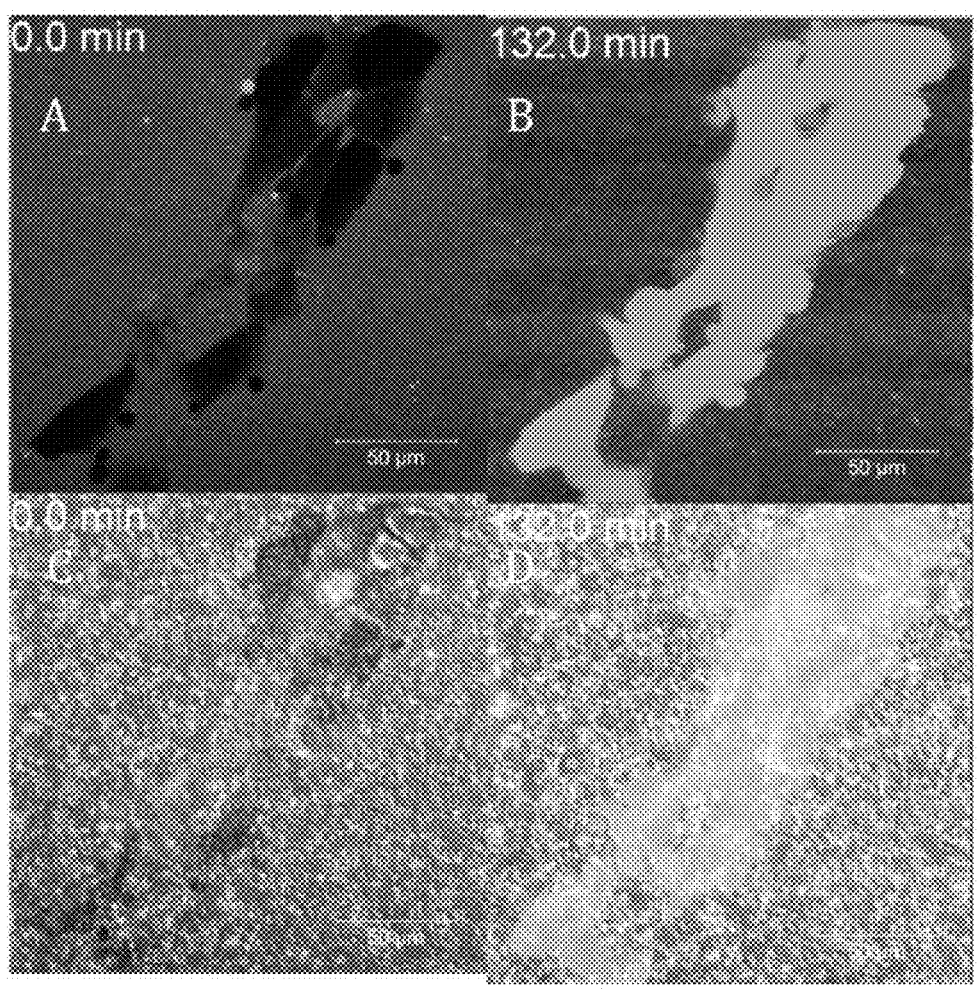
FIG. 12 shows: (A) a fluorescence image at 0 min; (B) a fluorescence image at 132 min; (C) a superposition of a transmission and fluorescence image at 0 min; and (D) a superposition of a transmission and fluorescence image at 132 min, showing rapid uptake of nBSA-FITC in the presence of unlabeled nGO by H12 cells.

In searching for a suitable explanation for the above observations where only nGO-FITC has been internalized but not other nanoparticles, we tested the possibility of nGO-assisted uptake of nanoparticles. The HN12 cells were exposed to a mixture of nBSA-FITC (0.3 mg/mL) and unlabeled nGO (0.3 mg/mL) and they have been imaged for uptake. Surprisingly, there has been very rapid uptake of nBSA-FITC in less than an hour (FIG. 12). For example, initially all the emission from the nBSA-FITC was located outside the cells (FIG. 12A), whereas intense emission was noted from inside the cells in less than 132 min of incubation (FIG. 12B). Overlay of the fluorescence images on the corresponding transmission images confirmed further that the emission is from within the cells (FIGS. 12C and 12D). Thus, nBSA-FITC which did not enter the cells by themselves were now readily internalized throughout the cytoplasm of the cells.

A likely explanation for this unexpected observation is that the culture media contained glucose, which is a substrate for nGO. The byproduct of glucose oxidation by nGO in the media would be hydrogen peroxide ($H_2O_2$), which is known to induce transient permeabilization of cell membranes and facilitate the uptake of certain ligands into the cells that are otherwise not internalized.

In control experiments, we tested the uptake of BSA-FITC in the presence of unlabeled GO, even though nBSA-FITC did not have any free BSA-FITC. Incubation of BSA-FITC with A549 cells for 4 h did not indicate any uptake. In another control experiment, the direct uptake of FITC in the absence of GO was tested, even though nBSA-FITC did not have any free FITC. Again, FITC is not internalized by A549 cells even after incubation for 4 h, which confirms that the uptake noted in FIG. 12 is due to the internalization of nBSA-FITC, not BSA-FITC, even in the presence of nGO, and there has been no direct uptake of FITC into the cells.

Since some control experiments were done with A549 cells but not HN12 cells, some explanation is essential. Both these cell lines have been used for a number of imaging studies. A recent review article comparing the uptake of carbon nanotubes by a wide range of cell lines concluded that the uptake depended on the charge and the size of the nanotubes, but not the cell types. Thus, it appears logical that HN12 and A549 cells would behave in a similar manner toward these nanoparticles.

Figure 13:
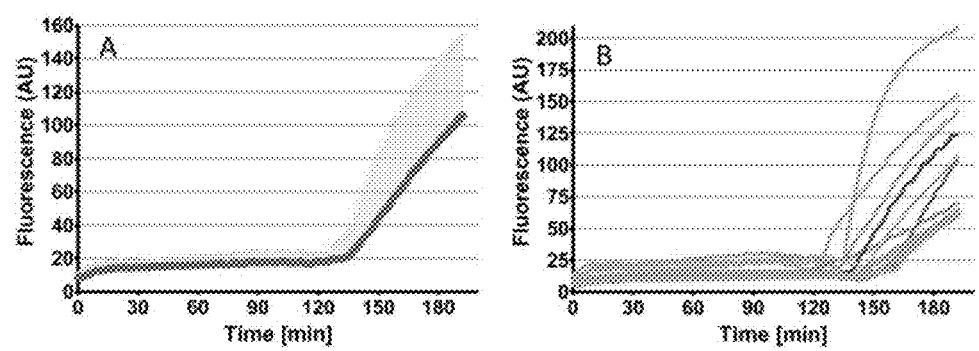
FIG. 13 shows graphs quantifying the time lapse in vivo imaging of nGO internalization by HN12 cancer cells: (A) average intracellular fluorescence intensity of 10 cells (bold line), and (B) fluorescence intensities from individual cells (AU=arbitrary units).

We analyzed the rates of internalization of nGO by live cells using time-lapse confocal microscopy and monitoring the emission intensity from particular cells as a function of time. Average fluorescence intensity from within the cells suddenly increased after 2-2.5 h of addition of nGO-FITC to the media, which suggested that the internalization of nGO has a lag phase (FIG. 13A). The intensity after ~200 min of incubation differed among different cells within the same culture, which is due to the differences in the uptake kinetics of individual cancer cells (FIG. 13B). Interestingly, nanoparticle internalization was accompanied by significant vesicular out-pocketing of the plasma membrane (blebbing), which may be an indication of a transient permeabilization of the plasma membrane.

To further test the role of nGO in the internalization of the nanoparticles, the HN12 cells were incubated for 2 h with nGOFITC and dextran Texas Red (MW 10,000 Da), which is normally introduced into the cells by microinjection. Internalization of both dextran Texas Red and nGO occurred concurrently, and internalization is accompanied by significant blebbing, both of which indicated transient permeabilization by nGO-FITC and cellular uptake of dextran Texas Red.

The extent of cellular uptake of nGO-FITC and dextran Texas Red was quantified by measuring the amounts of emission from within two individual cells at the corresponding emission wavelengths and plotted as a function of incubation time. The growth of dextran Texas Red followed that of nGO-FITC in both the cells, even though the kinetics and extent of uptake were not identical.

In another study, the HN12 cells were also incubated with a mixture of alexa555-Transferrin and nGO-FITC for 3 h. The cells were then washed with fresh media to remove unbound dyes, and the release of alexa555-Transferrin and nGO-FITC from within the cells has been monitored as a function of time. Plots show the simultaneous release of both samples from within the cells to the outside media, but nGO-FITC has been released more rapidly (nearly complete in about an hour). Note that none of the cells are killed by nanoparticles, on these time scales, which is likely because of their high degree of biocompatibility. These various uptakes as well as release studies clearly establish the utility of the nanoparticles for imaging. In addition, the increased permeability of the plasma membrane due to nGO in the media facilitated the uptake of dextran Texas Red and alexa555-Transferrin, whose uptake kinetics were concurrent with the uptake of nGO into the cells. Thus, the data unequivocally demonstrate the utility of the nanoparticles for cellular uptake and imaging.

Recent studies on the kinetics of nanoparticle uptake by cells show that uptake of Tat peptide conjugated QDs (Tat-QD) by HeLa cells takes place slowly and complete accumulation is achieved only after 24 h (Ruan et al. *J. Am. Chem. Soc.* 2007, 129, 14759). In another study, AuNPs were conjugated with oligonucleotides to promote their uptake; these indicated faster cellular uptake than the particles without the oligonucleotide label (Song et al. *Angew. Chem. Int. Ed.* 2009, 48, 8670). Single-walled carbon nanotubes, graphene oxide, and carbon dots (C-dots) were used for cellular imaging, but their uptake kinetics have been much slower than those of the nanoparticles (Xu et al. *Chem. Soc. Rev.* 2014, 43, 2560). For example, C-dots are taken up by human colon adenocarcinoma HT 29 cells only after overnight (Aiswal et al. Chem. *Commun.* 2012, 48, 407). Semiconducting nanoparticles resist photobleaching when compared to most organic dyes, but cytotoxic effects of the semiconductor nanoparticles are a concern (Heller et al. *Adv. Mater.* 2005, 17, 2793). C-dots, on the other hand, are less toxic and photostable, but they show very slow kinetics of cellular internalization (Cheng et al. *ACS Nano* 2008, 2, 2085).

In comparison to the existing nanoprobes, the nanoparticles described here have specific advantages, smaller size, higher stability, and long storage life, while retaining their biological activity to a significant extent, and these are promising alternatives as biocompatible tools for imaging. Nanoparticle surfaces could be decorated with affinity ligands that are capable of cell specific delivery with improved uptake efficiency for monitoring particle trafficking and localization. Current studies clearly demonstrate the potential of these nanoparticles as imaging agents and alternatives to other nanoparticles.

Example 2. Synthesis and Characterization of an Exemplary White Protein Fluorescent Nanoparticle Synthesis and Size Control of PNPs.

Protein solution was prepared by stirring 150 mg of BSA in 1 mL of de-ionized water ($dH_2O$). EDC (1M, $dH_2O$) was added in 10 mM aliquots and stirred for 20 min between additions. Particle growth was monitored by dynamic light scattering (DLS). Reaction was quenched by adding 1 mL of 20 mM $CO_3^{2-}/HCO_3^-$ pH 9.3 buffer. The resulting solution was diluted to 1 mg/mL in 100 mM phosphate 500 mM NaCl buffer pH 7.0, and heated to 85° C. for 10 min. The solution was allowed to cool back to room temperature on the bench. A solution of 1-pyrenebutanoic acid N-succinimidyl ester (P, 0.5% (m/m), 0.75 mg/mL, 1.9 mM) in DMSO was added to the protein solution and stirred for 2 h. Samples were filtered in Amicon 100 kDa cutoff centrifuge filter tubes with 10 mM $Na_2HPO_4$ pH 7.0 buffer until filtrate was clear of fluorescent dyes (approximately 6× sample volume). This method was repeated for making PNPs with the indicated fluorescent labels (5% m/m): 7-methoxycoumarin-3-carboxylic acid N-succinimidyl ester (M), 7-diethylaminocoumarin-3-carboxylic acid N-succinimidyl ester (D), fluorescein isothiocyanate (F), tetramethylrhodamine-5-(and-6)-isothiocyanate (T), and 5(6)-carboxy-X-rhodamine N-succinimidyl ester (R). White fluorescent GlowDots (W) were synthesized by adding F (0.19 mg/mL, 0.49 mM), M (2.15 mM, 0.68 mg/mL) and R (0.34 mg/mL, 0.54 mM) to 1 mL of nBSA in 10 mM $CO_3^{2-}/HCO_3^-$ pH 9.3, or by adding F (0.19 mg/mL, 0.49 mM), D (2.15 mM, 0.68 mg/mL) and R (0.34 mg/mL, 0.54 mM) to 1 mL of nBSA in 10 mM $CO_3^{2-}/HCO_3^-$ pH 9.3. Mol ratios of dyes were adjusted as needed until white fluorescence was observed. Reaction was stirred for 2 h and cleaned up by ultracentrifiltration (Amicon, 100 kDa) until filtrates were clear. All samples will be written using the following notation: $nBSA_W$ was also made by mixing particular ratios of $nBSA_M$, $nBSA_F$ and $nBSA_R$. Ratios were adjusted as needed until white fluorescence was achieved.

Dynamic Light Scattering (DLS).

Hydrodynamic radii of nBSA particles were monitored by means of photon correlation spectroscopy with Precision Detectors (Varian Inc.), CoolBatch+ dynamic light scattering apparatus with 10×10 $mm^2$ square cuvette, 658 nm excitation laser source with a 90° geometry. Data collection was done at room temperature, for 1 s, 3 repetitions with 200 accumulations. The PNPs, nBSA and BSA were filtered with 0.22 μm filter (PDVF, 13 mm, Restek). Precision Ellucidate v 1.1.0.9 and Precision Deconvolve v 5.5 were used to collect and analyze the data respectively Agarose Gel Electrophoresis.

Agarose gels were prepared by dissolving agarose (0.5% w/v, Sigma electrophoresis grade) in heated Tris acetate (40 mM, pH 7.0). The gel was poured on a horizontal electrophoresis apparatus (Gibco model 200, Life Technologies Inc., MD) and Tris acetate (40 mM, pH 7.0) was used as the running buffer. Samples were loaded into the wells at the center of the gel with 50% (v/v) loading buffer (50% v/v glycerol, 0.01% m/m bromophenol blue). Electrophoresis was carried out for 30 min at 100 mV at room temperature. The gel was stained overnight with 0.02% m/m Coomassie Blue, 10% v/v acetic acid and then destained overnight with 10% v/v acetic acid. This procedure was repeated with 40 mM Tris acetate buffer with lower pH to determine the pI of PNPs.

Circular Dichroism (CD).

CD spectra were measured on a Jasco J-710 CD spectrometer. A concentration of 1.25 µM protein in 10 mM $Na_2HPO_4$ pH 7.0 was used. Spectra were obtained using a 0.05 cm path length quartz cuvette in the region of 260-190 nm. Other operating parameters were: sensitivity 100 mdeg, data pitch 0.5 nm, continuous scanning mode, 50 nm/min scanning speed, 1 s response, 1.0 nm bandwidth and 3 accumulations. CD spectra were corrected by subtracting buffer signal from sample signal. Enzyme structure retention was assessed by calculating the change in ellipticity where BSA in 10 mM $Na_2HPO_4$ pH 7.0 was taken as 100% ellipticity.

Zeta Potential.

Zeta potential were measured on a Brookhaven Instruments Zeta Plus analyzer using the software from the manufacturer. Charge on, nBSA and BSA were measured in 10 mM $CO_3^{2-}/HCO_3^-$ pH 9.3 buffer with 0.1 M KCl added to the sample. Measurements were done at room temperature and 3 scans collected for each sample.

SDS PAGE.

A 7% separating with 5% stacking gel was used. Samples were prepared by adding loading buffer (10 µL, 2% SDS, 10% BME) to the sample then boiled for 2 minutes. Samples were loaded into the gel so that each well contained 6 µg of protein. The gel was run in SDS running buffer at 200 V constant in Bio-Rad Mini Protean Electrophoresis apparatus until the dye front was 1 cm from the bottom of gel plate. Gel was stained in Stain I (10% v/v acetic acid, 10% v/v isopropanol, 0.02% Coomassie blue) for 1 h. Gel was then placed in Stain II (10% v/v acetic acid, 0.02% Coomassie blue) overnight. The gel was destained in 10% v/v acetic acid until bands were clearly distinguished from clear background of gel.

Native PAGE.

A 7% separating and 5% stacking gel was used in the Native PAGE. Samples were prepared by adding loading buffer (10 µL, 0.31 M Tris HCl pH 6.8, 0.05% Bromophenol blue, 50% glycerol). Samples were loaded into the gel so each well contained 6 µg of protein. Gel was run in electrophoresis buffer (24.8 mM Tris, 191.8 mM Glycine pH 8.3) at 200 V constant in Bio-Rad Mini Protean Electrophoresis apparatus until the dye front was 1 cm from the bottom of gel plate. Gel was stained by same method mentioned above in SDS gel procedure.

Transmission Electron Microscopy (TEM).

The nano particle suspension (0.2 mg/mL) was applied to a carbon-coated Cu grid (400-mesh) after treating the grid with a plasma cleaner (Harrick PDC-32G). Aliquots of 3 µL were incubated on the grid for 60 s, blotted with filter paper (Whatman #4), and stained with 3 µL of 1% uranyl acetate for 30 s followed by blotting. After an hour of drying, the grids were imaged using a FEI Tecnai Spirit TEM with an operating voltage of 80 kV and a mounted digital camera.

Spectral Measurements.

Absorption spectra were measured on an HP 8450 diode array spectrophotometer (Varian Inc., Santa Clara, Calif.). Samples were diluted to 0.412 in 10 mM $Na_2HPO_4$ pH 7.0 and the baseline averaged from 700-800 nm was subtracted. Fluorescence spectra were recorded. Samples were diluted to approximately 0.4 mg/mL by protein, in 10 mM $Na_2HPO_4$ pH 7.0 and a filter with cutoff below 300 nm used on the emission side. All spectral measurements were done in a 1×1 $cm^2$ quartz cuvette.

Temperature Stability Studies.

Effects of temperature measured by recording the absorption spectrum, fluorescence spectrum and CD of $nBSA_W$. A solution of white fluorescent protein nano particles ($nBSA_W$) (0.412 mg/mL in 10 mM $Na_2HPO_4$ pH 7.0) was placed in a thermo cell with constant stirring. The temperature of the cell was increased by 5° C. and the sample allowed to equilibrate for 4 min after the cell reached temperature. Spectra were recorded for temperatures 25-85° C. The absorbance spectrum was collected from 260 nm to 700 nm and the baseline at 700 nm subtracted from it. $nBSA_W$ was placed at 4° C. overnight and allowed to equilibrate to room temperature and the spectrum recorded. The fluorescence and CD spectra were also recorded for this sample and compared to spectra before heating.

Differential Scanning Calorimetry (DSC).

Thermal denaturation of PNPs was performed on a Nano II Differential Scanning Calorimeter (model 6100, CSC, Utah). BSA and $nBSA_W$ solution (in 10 mM $Na_2HPO_4$ pH 7.0) were scanned from 25-90° C. with 1° C./min. The specific heat of the samples was recorded with respect to the sample cell (10 mM $Na_2HPO_4$ pH 7.0). Excess molar heat capacities were calculated using molar mass of BSA. Peak transition temperature ($T_m$), the temperature where denaturation begins, and $\Delta H_{denaturation}$ (integral $C_p dT$) were extracted from DSC data using CpCalc Analysis software.

Results.

Reported here is the synthesis of multi-colored and white emitting protein nanoparticles in a simple and facile approach. Both the size and the size distributions of the particles are controlled by adjusting the reaction conditions. The particles are labeled with fluorescent dyes for controlling their optical properties. The dyes cover the absorption range of 300 to 600 nm and emit from 340 to 650 nm. The white emitting particles are produced by a combination of three or more dyes attached to the same particle so that the net emission from the particles is white. White emitting particles were also produced by mixing the blue, green and red emitting particles in appropriate combinations and these can be used for multiplexed imaging. Thus, both types of white emitting particles are made and the details are provided below.

Synthesis of PNPs. In this method, the carboxylic groups of BSA molecules were crosslinked with the amine groups of other BSA molecules. High concentrations used in synthesis procedure result in aggregation of the protein. The aggregated proteins were then crosslinked with other proteins in the aggregated particle via carbodiimide chemistry. This particle formation was monitored via DLS. Once the desired sizes and ratios were achieved, the particle formation was quenched by adding carbonate buffer. These protein nanoparticles were then decorated with fluorescent labels. Final products were monitored by DLS, agarose electrophoresis, and TEM. The resulting samples were thoroughly characterized by physical and biochemical methods. Particle formation was controlled by concentration of EDC and fluorescent labels used. For example, samples with 70% 9 nm and 30% 50 nm particles were synthesized with 20 mM EDC over 1 h stirring time.

Figure 14:
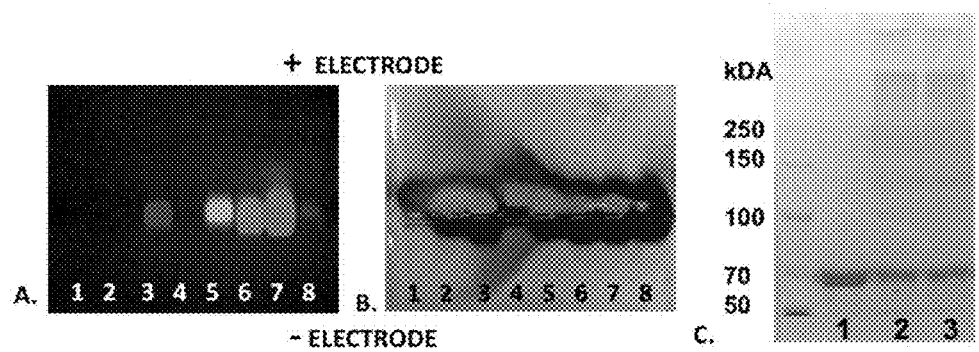
FIG. 14 shows gel electrophoresis images of nBSAx particles (where x=various fluorophores as described in Example 2). (A) Gel under a UV lamp (254 nm), lane 1=BSA, lane 2=nBSA, lane 3=nBSA$_P$, lane 4=nBSA$_M$, lane 5=nBSA$_F$, lane 6=nBSA$_T$, lane 7=nBSA$_R$, and lane 8=nBSA$_W$. (B) Coomassie stain image of the same gel as in (A). (C) SDS-PAGE gel, lane 1=BSA, lane 2=nBSA, lane 3=nBSA$_W$.
Figure 15:
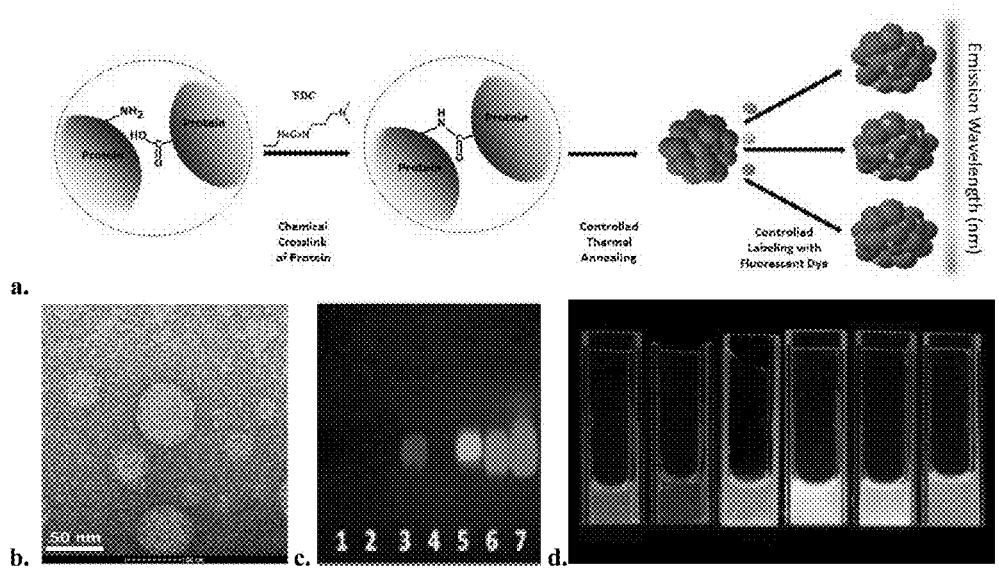
FIG. 15 shows: (A) a scheme showing a method of synthesis of multicolored particles; (B) a TEM image of protein nanoparticles of approximately 40 nm in diameter; (C) a fluorescent agarose gel (40 mM Tris Acetate pH 7) imaged under UV light, in which bands in lanes 3-7 are blue, blue, green, red and red respectively; and (D) solutions fluorescing under 254 nm irradiation, wherein the vials are light blue, royal blue, blue-green, green, yellow and orange in color from left to right.

Gel Electrophoresis. Agarose gel of nBSA and $nBSA_P$, $nBSA_M$, $nBSA_F$, $nBSA_T$ $nBSA_R$ and $nBSA_W$ was imaged using UV light (254 nm, FIG. 14A). nBSA labeled with 5 different dyes was easily seen by the UV light. Dyes used in synthesis those described above (P, M, F, T and R, lanes 3-8 respectively). Slight increase in mobility was seen in PNPs labeled with M (lane 4). No detectable amounts of free dye were seen in any of the lanes. The same gel was Coomassie stained to reveal protein bands. The fluorescent spots lined up with the Coomassie stained protein bands showing the PNPs were labeled with the dye. Free BSA (lane 1) traveled further towards the positive electrode compared to nBSA (lane 2). The decreased mobility was due to increased size of the protein nanoparticle. Labeling nBSA with P, F, R, T and W resulted in no changes in migration distance (lanes 3, 5-8 respectively).

SDS (FIG. 14C) and native PAGE (not shown) were used to better understand the composition of the $nBSA_X$ samples. SDS-PAGE (FIG. 14C) showed wells containing nBSA (lane 2) and $nBSA_W$ (lane 3) had both free protein (bottom band, approx. 66 kDa) and crosslinked protein (middle band, approx. 140 kDa and top smear, too large to calculate). Smearing is common is samples that are crosslinked. Free BSA was shown in lane 1 for comparison. Results of Native PAGE are similar with samples of nBSA and $nBSA_W$ showing both free BSA and smeared bands of crosslinked BSA.

Sizes of PNPs. Dynamic light scattering was measured to determine the size of PNPs after labeling with fluorescent dyes. BSA in 10 mM $Na_2HPO_4$ pH 7.0 showed an average diameter of 3 nm (70%) with some larger aggregates of 50 nm (30%) present. After formation of nBSA, a distribution of 9 nm (70%) and 50 nm (30%) was observed. No free BSA was detected in the samples. Labeling with the dyes F, T, R and W did not result in changes in the size and distribution of the particles. However, nBSA labeled with P and M showed larger aggregates in solution. Data are summarized in Table 5.

TABLE 5

DLS Data for Protein Nanoparticles

| Sample | Size 1 | Size 2 | Size 3 | Size 4 |
|---|---|---|---|---|
| BSA | 3 nm (65%) | 64 nm (37%) | — | — |
| nBSA | 10 nm (70%) | 75 nm (30%) | — | — |
| $nBSA_P$ | 8 nm (38%) | 47 nm (29%) | 310 nm (33%) | — |
| $nBSA_M$ | 6 nm (14%) | 59 nm (32%) | 191 nm (22%) | 1126 nm (32%) |
| $nBSA_F$ | 8 nm (52%) | 59 nm (48%) | — | — |
| $nBSA_T$ | 9 nm (59%) | 62 nm (41%) | — | — |
| $nBSA_R$ | 8 nm (50%) | 55 nm (50%) | — | — |
| $nBSA_W$ | 9 nm (40%) | 35 nm (55%) | — | — |

The DLS data was supported by TEM micrographs of $nBSA_W$. Particles can clearly be seen to have a diameter of approximately 10 nm, confirming the particle size observed by DLS.

Protein Secondary Structure and Charge. Native structure of protein is vital for biological activity retention. The structure of the BSA in PNPs was analyzed via circular dichroism and compared to free BSA to determine if any loss in structured occurred. The far UV-CD spectra for BSA showed double minima at 222 and 208 nm with one maxima at 195 nm. Upon formation of nBSA and $nBSA_W$, no change in spectral shape or intensity was observed.

Zeta potential of BSA, nBSA and $nBSA_W$ was measured to observe any changes in particle charge due to protein particle formation and labeling with fluorescent dye. Zeta potential Studies revealed an increase in net charge of nBSA (+50 mV), a drastic increase from BSA (−14 mV). Upon labeling of nBSA with M, F, R to obtain white fluorescence ($nBSA_W$), the zeta potential decreased slightly (+35 mV).

Figure 16:
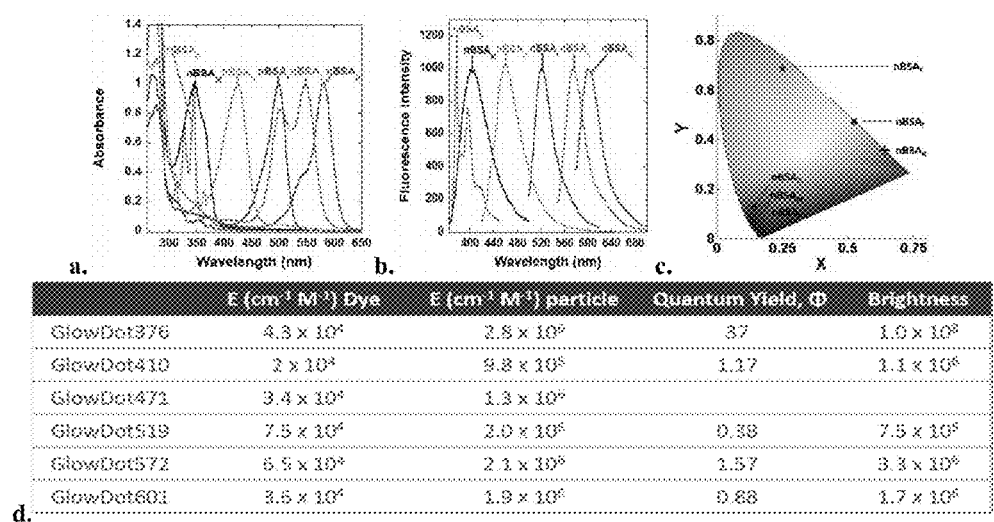
FIG. 16 shows absorbance and fluorescence spectra: (A) absorbance spectra of six nanoparticle samples; (B) fluorescence of six nanoparticle samples; (C) chromaticity coordinates of six nanoparticle samples; and (D) excitation, quantum yield, and brightness values calculated for each nanoparticle sample.
Figure 17:
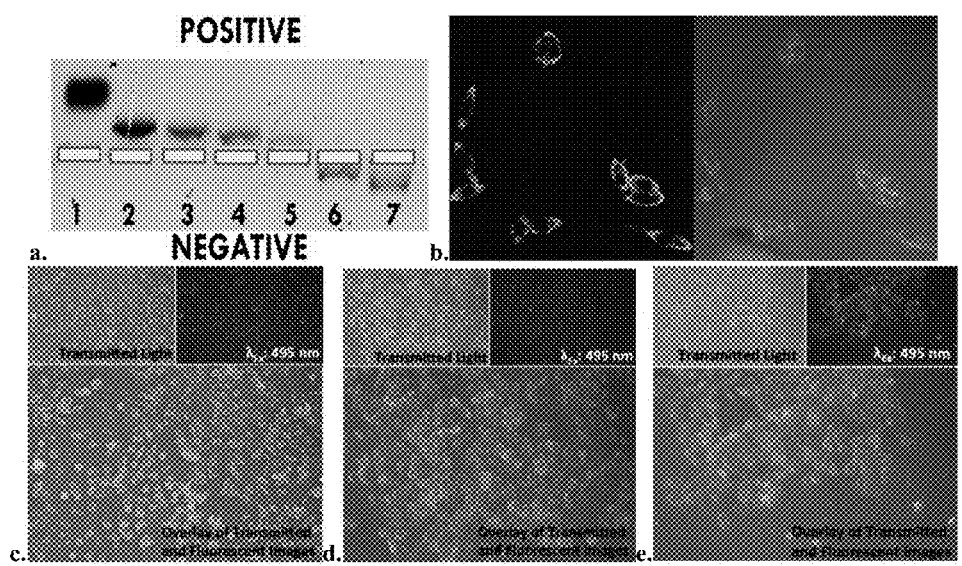
FIG. 17 shows images of PNPs modified with taurine for cellular uptake: (A) an agarose gel of certain PNPs; (B) cellular uptake observed when GlowDot494 is coincubated with HeLa cells for 3 hours; and cell uptake of GlowDot494 after coincubation with MDAMB (C), PC3 (D), and L6 (E) cells after 3 h.
Figure 18:
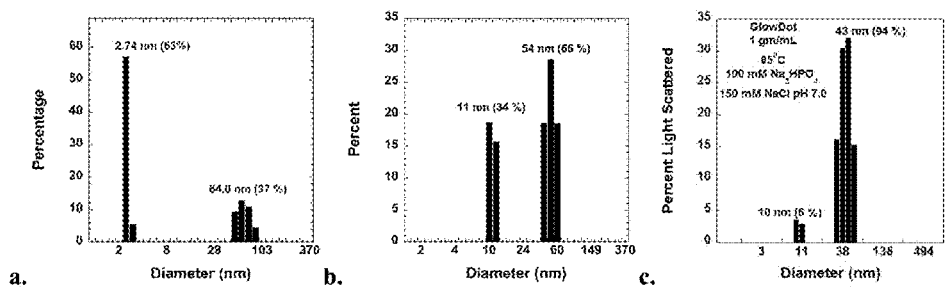
FIG. 18 shows changes observed in DLS from: (A) beginning; (B) before annealing; and (C) after annealing steps of nanoparticle synthesis.
Figure 19:
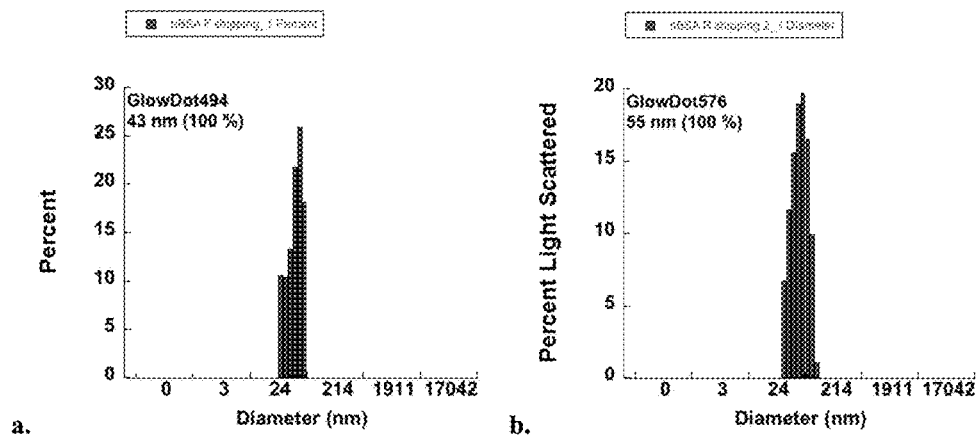
FIG. 19 shows DLS data for two examples of purified PNPs: (A) GlowDot494; and (B) GlowDot576.
Figure 20:
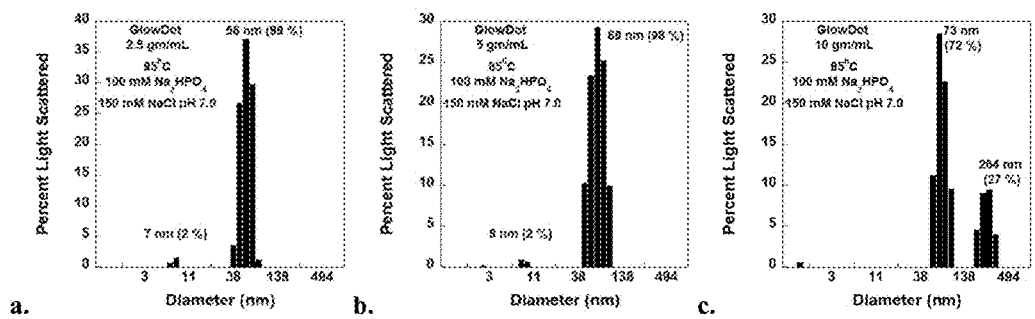
FIG. 20 shows DLS spectra demonstrating control over particle size through the synthesis parameter of concentration, used during the annealing step.
Figure 21:
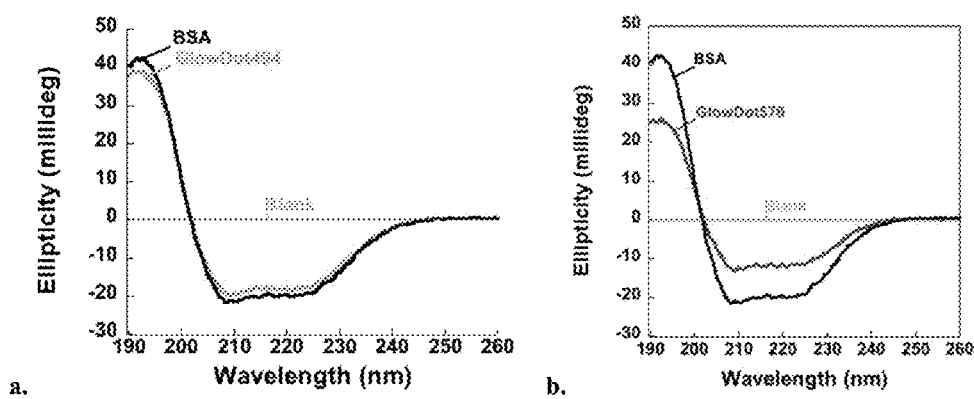
FIG. 21 shows CD spectra demonstrating retention of protein structure after synthesis of GlowDot 494 (A) and GlowDot576 (B).
Figure 22:
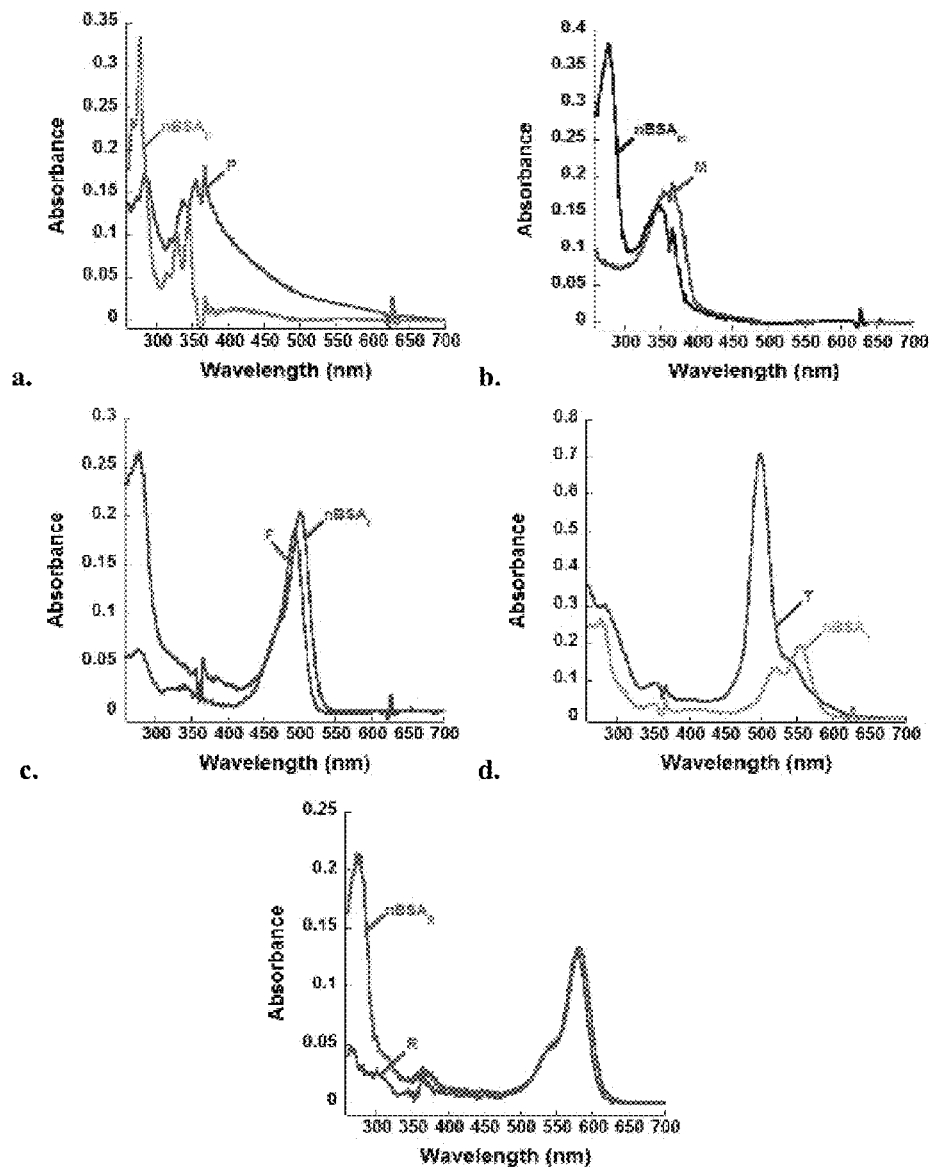
FIG. 22 shows changes in absorbance spectra of free dyes compared to the dyes bound to nBSA nanoparticles for: (a) 1-pyrenebutanoic acid N-succinimidyl ester (P); (b) 7-methoxycoumarin-3-carboxylic acid N-succinimidyl ester (M); (c) fluorescein isothiocyanate (F); (d) tetramethylrhodamine-5-(and-6)-isothiocyanate (T); and (e) 5(6)-carboxy-X-rhodamine N-succinimidyl ester (R).

Spectroscopic Properties. Absorbance properties of PNPs were evaluated by UV-Visible spectroscopy and fluorescence spectroscopy. Absorbance of PNPs span the visible spectrum as seen in FIG. 16A. $nBSA_P$ showed two absorbance peaks at 325 and 340 nm. The second absorbance peak of $nBSA_P$ was overlapped by the broad absorbance peak of $nBSA_M$ at 358 nm. $nBSA_F$ absorbed 495 nm and was overlapped by the absorbance of $nBSA_T$ which showed two absorbance peaks at 490 nm and 550 nm. $nBSA_R$ absorbed the longest wavelengths of the bunch with an absorbance at 575 nm. In all samples, the absorbance of BSA was seen at 280 nm. The fluorescence emission of each dye, when excited by its respective absorbing wavelength, followed the same trend as shown in FIG. 16B (X=P, M, F, T, R, at 400, 400, 520, 575, and 601 nm respectively). $nBSA_P$ had two fluorescence emission peaks, at 375 and 400 nm. $nBSA_M$ had a single fluorescence emission peak at 400 nm that is broad. $nBSA_F$ had emission at 520 nm. $nBSA_T$ had only one emission wavelength at 571 nm despite having two absorbance peaks. $nBSA_R$ has one emission peak at 601 nm and was the longest wavelength emitting PNPs.

Absorbance and fluorescence of $nBSA_W$ was also studied by UV-Vis and fluorescence spectroscopy. $nBSA_W$ was synthesized by adding F, M, and R to the same solution. As shown in FIG. 16C, the absorbance spectra clearly showed peaks corresponding to BSA, M, F, and R absorbance (280, 358, 495, and 575 nm, respectively). The intensity of M and F absorbance were very similar (0.2 Au) however intensity of R absorbance was less (0.8 Au). Fluorescence spectrum was collected for the sample when excited at 254 nm, as shown in FIG. 16D. The spectra resulted in large emission peaks for BSA and M (354 and 400 nm, respectively). A smaller emission peak was seen at 520 nm for F. The furthest peak, 601 nm, corresponded to fluorescence emission of R. Both F and R showed significantly less intense fluorescence emission when excited at 254 nm. The same sample was excited at the absorbance wavelength for each of the dyes used in the synthesis. When excited at 358 nm (M absorbance nm), large emission was seen from M, and near no emission from F and R. Excitation of $nBSA_W$ at 495 nm (F absorbance nm) resulted in one large emission peak at 520 nm and nearly no emission from R. Excitation of $nBSA_W$ showed one large emission peak at 601 nm corresponding to R. Spectra were normalized to the same dye intensity so comparison could be made. All spectra were collected with 0.412 mg/mL protein in 10 mM $Na_2HPO_4$ pH 7.0.

Temperature Stability.

Figure 23:
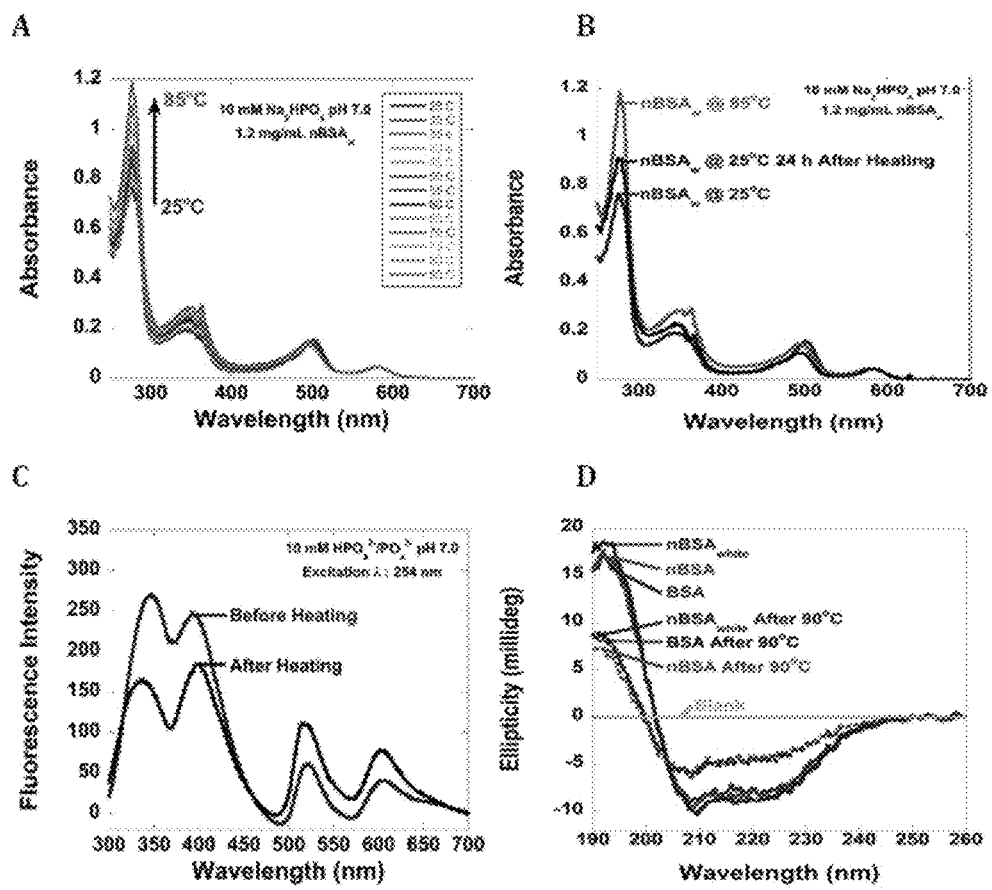
FIG. 23 shows: (a) absorbance spectra of white PNPs as a function of temperature; (b) absorbance spectra of white PNPs initially at 25° C., then at 85° C., and 20 hours after cooling back to 25° C.; (c) fluorescence emission spectra of white PNPs before and after heating; and (d) CD spectra of white PNPs and BSA before and after heating.

Temperature stability of PNPs was measured by UV-Vis spectroscopy, fluorescence spectroscopy, and circular dichroism. Sample of $nBSA_W$ was heated to 85° C. and the absorbance spectra collected as a function of time (FIG. 23A—0.412 mg/mL in 10 mM $Na_2HPO_4$ pH 7.0). Four peaks were initially seen at 25° C., BSA (280 nm), M (358 nm), F (495 nm) and R (575 nm). As the temperature increased, BSA absorbance increased drastically with a 0.2 Au increase over the temperature range used. The absorbance of M also increased with temperature, however not as drastically (0.1 Au increase). The small shoulder on the red side of the peak was an artifact of the instrument switching lamps from UV to visible. Peak at 495 nm (F) remained unchanged up to 45° C. As the temperature was increased, its absorbance to decreased and blue shift. At 70° C., the absorbance increased again while continuing to blue shift. At 85° C., the peak of F had shifted 5 nm towards the blue end of the spectrum. The peak at 575 nm (R) remained unchanged at all temperatures. The sample was allowed to cool back down overnight and the spectrum collected and compared to its initial absorbance at 25° C. before heating and its spectrum at 85° C. during heating (FIG. 23B). The absorbance of BSA (280 nm) after cooling dropped approximately halfway between the absorbance at 25° C. before heating and the absorbance at 85° C. No shift in peak absorbance was noted. The absorbance of M (358 nm) also decreased after cooling but not enough to return it to its normal spectra. The peak at 495 nm (F) remained blue shifted by 5 nm and the intensity decreased compared to both 25° C. before heating and 85° C. absorbance. Absorbance of R (575 nm) remained unchanged at all conditions of the experiment.

The fluorescence emission (ex: 254 nm) of nBSA$_W$ (0.412 mg/mL in 10 mM Na$_2$HPO$_4$ pH 7.0) heated to 85° C. was also collected and compared to the fluorescence emission spectra before heating (FIG. 23C). Before heating, the intensity of emission peaks of BSA and M (354 and 400 nm, respectively) were 4-5× greater than the peaks of F and R (520 and 601 nm respectively). After heating, the intensity of BSA and M were less than 2× greater than the intensity of F and R. Visual inspection of the sample excited at 254 nm shows that the sample is still fluorescing white.

The CD spectra were collected to determine the proteins stability to high temperatures (FIG. 23D, 1.25 µM protein in 10 mM Na$_2$HPO$_4$ pH 7.0). Before any heating, BSA, nBSA, and nBSA$_W$ all showed nearly identical CD spectra with double minima at 222 nm and 208 nm and one maxima at 195 nm. After heating to 90° C. for 10 min, a loss in ellipticity was seen for BSA, nBSA and nBSA$_W$ when compared to their unheated spectra. However, little change was seen between BSA, nBSA and nBSA$_W$ heated samples.

Thermodynamic Properties. The thermodynamic properties of nBSA$_W$ were investigated by differential scanning calorimetry and compared to BSA. The specific heat at contestant pressure was plotted as a function of temperature. BSA had a peak at approximately 65° C. signifying the temperature at which BSA denatures. nBSA$_W$ showed an initial broad peak at approximately 63° C. with a second small, broad peak at 83° C.

Cellular Uptake Studies. The cellular uptake of nBSA$_F$ was investigated. When added to HN12 oral cancer cells, no cellular uptake of nBSA$_F$ was observed. When added to the cells along with protein nanoparticles composed of glucose oxidase (nGO), rapid cellular uptake was observed. These results were confirmed with a second cell line, A549.

Discussion.

Synthesis of PNPs was achieved via EDC chemistry and fluorescent labeling. Agarose gels of nanoparticles show that a wide range of emission wavelengths is achievable. No free dye is seen in the agarose gel. Clean up for nanoparticles is minimal due to excellent efficiency of the labeling step. SDS gel confirms that particles are composed of both crosslinked protein and single protein molecules that are associated with the crosslinked portions of Proteos.

Particle formation was monitored and confirmed by dynamic light scattering (DLS) and transmission electron microscopy (TEM). DLS showed BSA had two predominate sizes in solution; a 3 nm diameter particle (65% abundance) corresponding to free BSA and another larger particle of 64 nm diameter (37% abundance), corresponding to aggregated BSA. DLS of nBSA showed two sizes present. The most abundant particle size was 10 nm in diameter, corresponding to approximately 3 BSA molecules in the particle. The larger peak was 75 nm, corresponding to approximately 23 BSA molecules in the particles. DLS showed clean peaks with narrow distribution. No 3 nm diameter particles were detected by DLS suggesting that the single BSA molecules associated with crosslinked particles were very tightly associated. Upon labeling with fluorescent dyes, some shifts in abundance of the two sizes were seen for nBSA$_F$, nBSA$_T$, nBSA$_R$, and nBSA$_W$, however the general trend of a bimodal system with 10 nm and 50 nm particles remained. Unique in the synthesis of nBSA$_P$ and nBSA$_M$, some larger aggregates were detected in DLS. The aggregation is thought to have been due to the dyes. The size of nBSA$_W$ was confirmed by TEM. Images showed dark backgrounds with white spots. These spots were nBSA$_W$. The few isolated molecules appeared to be approximately 10 nm in diameter.

Zeta potential of Proteos was recorded and compared to nBSA and BSA. In 10 mM CO$_3^{2-}$/HCO$_3^-$ pH 9.3, BSA showed a zeta potential of −14 mV. This is a reasonable charge for BSA at high pHs where all amino acids are protonated. nBSA had a drastic shift in zeta potential, +50 mV. Synthesis of nBSA involves conversion of carboxylic acid groups and amine groups into amide bonds. There is no reason to suggest that this reaction should create a drastic change in protein surface charge. Zeta potential of nBSA suggested that there was something beyond our understanding occurring in the system. nBSA$_W$ showed a slight decrease in zeta potential, +30 mV, which was most likely caused by the addition of fluorescent dyes to the positively charged amine groups.

The circular dichroism (CD) spectrum of nBSA$_W$ was collected and compared to the CD spectra of nBSA and BSA to better understand the effect particle formation had on the protein's secondary structure. The spectrum of BSA showed double minima at 222 and 208 nm and one maxima at 198 nm, indicating an alpha helix structure. This same spectral shape was noted for both nBSA and nBSA$_W$, leading to the conclusion that formation of protein nano particles and labeling with fluorescent dyes had no effect on the secondary structure. This is an important property of the synthesis for the future use of other proteins. The catalytic activity of protein is related to its secondary structure. Having a synthesis that does not harm the protein structures means that this synthesis can be expanded to other proteins that may have desirable catalytic activities. The use of a very similar synthesis procedure showed preservation of protein structure and catalytic activity of other proteins used in protein nanoparticles.

Absorbance and fluorescence spectra of samples were collected. Proteos emission wavelengths spanned the entire visible spectrum. Shown in this paper were the following emission wavelengths: 350, 400, 520, 575 and 601 nm. Other emission wavelengths should be possible with this system. Quantum dots have a wide range of emission wavelengths available, stretching from UV to IR range, and are now capable of white fluorescence. Proteos have now successfully achieved emission wavelengths ranging the visible range and white light fluorescent.

Thermal stability of Proteos was investigated using UV-Visible Spectroscopy, circular dichroism, and DSC. The absorbance spectra of nBSA$_W$ was plotted for different temperatures. As the temperature was increased, BSA absorbance also increased. This is expected as BSA denatures at high temperatures. There was also an increase in the absorbance of M. Absorbance peak of F initially decreased up to 45° C. before blue shifting while simultaneously increasing above 45° C. At 90° C., the peak absorbance of F had shifted 5 nm below its original position. The absorbance of R remained unchanged for all temperatures. Only these minor changes were observed in the UV Visible spectrum at high temperatures. After being allowed to cool back to room temperature, it was visually checked with a hand held UV lamp (254 nm emission). The white fluorescence of the particle remained intact after being heated to 90° C.

The white fluorescence was confirmed by the fluorescence spectrum of the heated then cooled sample of nBSA$_W$. All peaks present in the sample before heating were still easily seen in the spectrum after heating to 90° C. and cooling. However, the ratios of individual dye peaks to each other was changed. Overall, there was a drop in intensity of BSA and M fluorescence while F and R increased slightly in intensity. The CD spectra of samples heated to 90° C. for 10 minutes and then cooled back to room temperature show a 52% retention in structure after heating. Similar retention in structure is seen for nBSA and BSA samples suggesting that the Proteos do not have any increased retention in structure at high temperatures.

Thermo dynamic data was collected for BSA and nBSA. BSA was found to have a melting temperature of approximately 64° C. $nBSA_W$ had two different melting temperatures, 61° C. and 82° C. The two melting temperatures noted in $nBSA_W$ could be due to the system being composed of both associated protein that melted at 61° C. and crosslinked protein that melted at 82° C. Protein nanoparticles' fluorescence properties are highly thermally stable while their secondary structure show improved thermal stability compared to native protein. Long term storage of Proteos is still being investigated and must be addressed in order to compete with quantum dots. Quantum dots with passivated surfaces have excellent thermal stability.

Cellular uptake of precursors to Proteos was previously published. Protein nano particles made with BSA and FITC ($nBSA_{FITC}$) were not taken up by cells after 2.2 h. However, when protein nano particles made with glucose oxidase (nGO) were added to cells with $nBSA_{FITC}$ and glucose, rapid cellular uptake was seen after 2.2 h. Fluorescence could be seen throughout the entire cell showing that the nano-particles go into all parts of the cell. nGO is required for internalization of protein nano particles. Quantum dots also required aid in entering the cell. Due to their lack of biocompatibility, some method of passivation is required in order to make them water soluble, decrease their toxicity and prevent them from being taken up by endocytosis.

Example 3. Additional Synthesis and Characterization of an Exemplary White Protein Fluorescent Nanoparticle White-emitting nanoparticles were prepared in an analogous manner to the white fluorescent PNPs (W) described in Example 2, i.e. by first stirring 150 mg of BSA in 1 mL $dH_2O$, and then adding EDC (1M in $dH_2O$) in 10 mM aliquots and stirring for 20 min between additions. Particle growth was monitored by DLS, and the reaction was quenched by adding 2 mL of 15 mM $CO_3^-/HCO_3^-$ pH 9.3 buffer. In this case, uniform particle sizes were achieved by slowly heating 1 mg/mL solution to 85° C. and allowing to slowly cool back to room temperature. The white fluorescent particles were then synthesized by adding F (0.19 mg/mL, 0.49 mM), M (2.15 mM, 0.68 mg/mL) and R (0.34 mg/mL, 0.54 mM) to 1 mL of nBSA in 10 mM $CO_3^{2-}/HCO_3^-$ pH 9.3. Mol ratios of dyes were adjusted as needed until white fluorescence was observed. The reaction was stirred for 2 h and purified by ultracentrifiltration (Amicon, 100 kDa) until filtrate was clear. White emitting particle solution was also synthesized by mixing molar ratios of nBSA350, nBSA494 and nBSA576. Ratios of GlowDots were adjusted as needed until white fluorescence was achieved. nBSAW405T was synthesized by labeling the particles with Taurine (1 mg/mL BSA, 1.5 mM Taurine, and 160 mM EDC added last) before the annealing step. During the labeling process, M was replaced with 6-diethylaminocoumarin-3-carboxylic acid N-succinimidyl ester (D). All other parameters were the same.

Particles were characterized using DLS, agarose gel electrophoresis, CD, SDS-PAGE, TEM, and other spectral measurements in manners similar to those set forth in Examples 1 and 2.

For cell imaging studies in HeLa cells, HeLa cells were grown in DMEM at 37 C 5% $CO_2$ for 24 hours in an 8 well chamber with cover plate bottoms. To each well of cells, 0.3 mg/mL nBSAW405T was added. Samples were incubated at 37 C and 5% $CO_2$ for 3 hours. Imaging was done on a Nikon MR confocal microscope. Blue channel was excited by a 405 nm diode laser and monitored at 461 nm. The green channel was excited with 488 argon laser and monitored at 525 nm. The red channel was excited by a 588 nm argon laser and monitored at 595 nm. All images were processed with FIJI (Fiji Is Just ImageJ).

Figure 24:
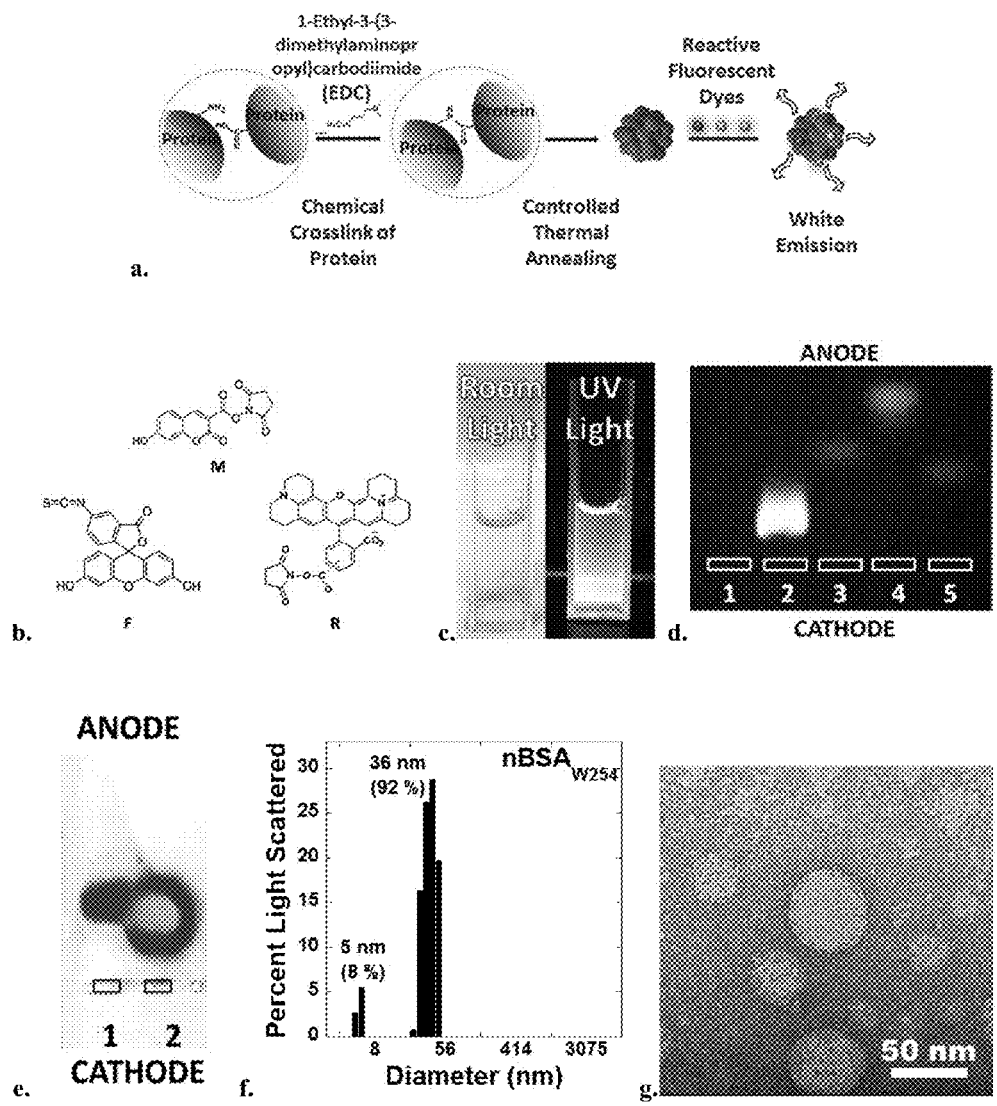
FIG. 24 shows: (a) a scheme illustrating covalent conjugation of a protein with a carbodiimide and subsequent labeling with multiple fluorescent dye reagents to produce a white fluorescing nanoparticle; (b) structures of certain fluorescent dye reagents; (c) white emission under UV light; (d) a fluorescence image an agarose gel of white PNPs and other dyes; (e) an image of the gel in (d) with Coomassie Blue stain; (f) DLS of white PNPs; and (g) TEM of white PNPs.
Figure 25:
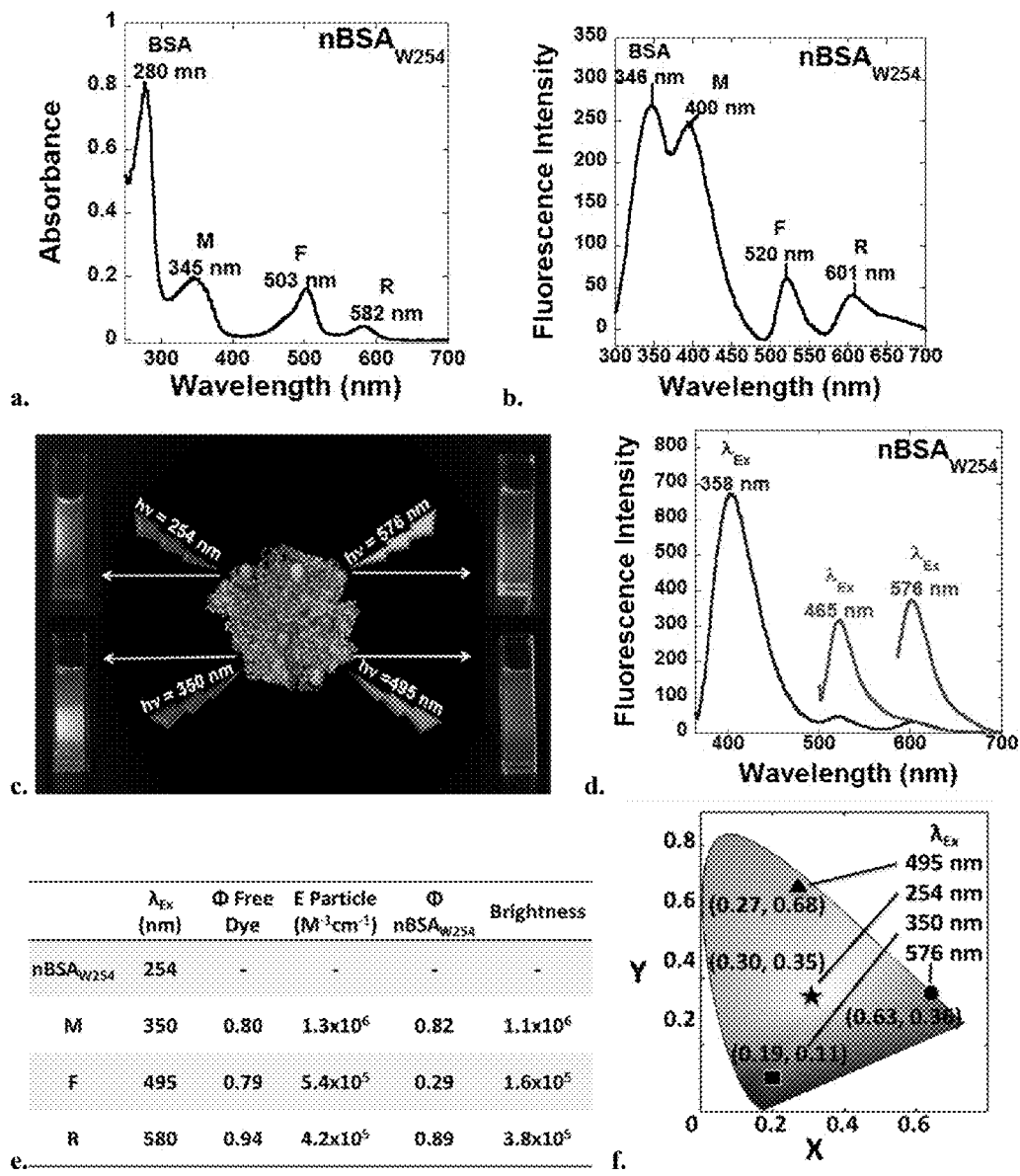
FIG. 25 shows: (a) absorption spectrum of white PNPs; (b) fluorescence emission spectrum of white PNPs when excited at 254 nm; (c) multi-mode excitation and emission of white PNPs; (d) emission spectra of white PNPs with different excitation wavelengths; (e) quantum yields and color coordinates of white PNPs; and (f) chromaticity plots of white PNPs with different excitation.

Characterization data is shown in FIG. 24 and FIG. 25.

Figure 26:
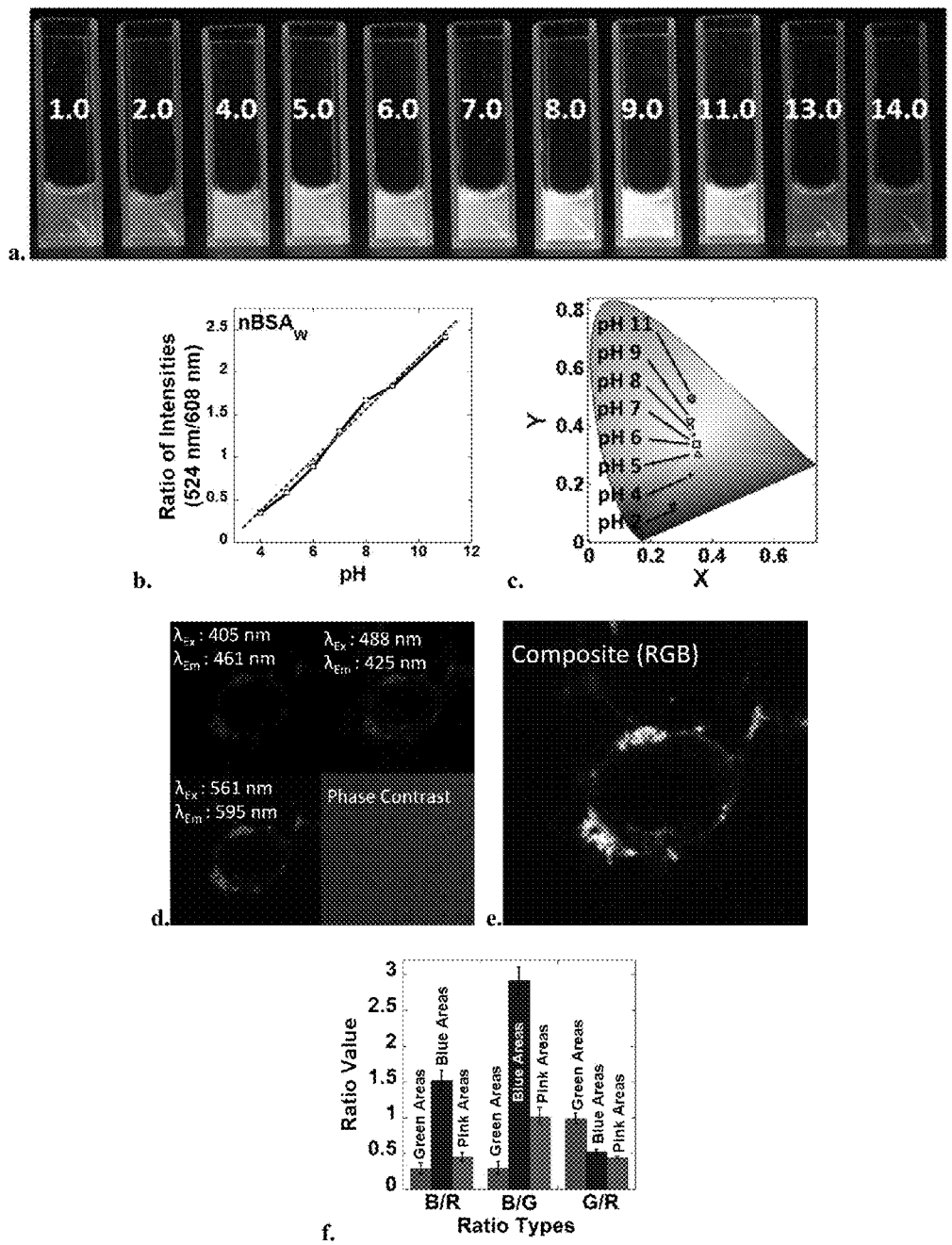
FIG. 26 shows: (a) sensitivity of the chromaticity of white PNPs to pH, where fluorescence is white at pH. 7.0-9.0, yellow at 11.0, green at 13.0, and nearly quenched at 14.0, while fluorescence at pH. 1.0-6.0 is varying shades of purple to pink; (b) ratio of fluorescence intensities at 524 nm and 608 nm for white PNPs as a function of pH from 4-11; (c) changes in fluorescence color as a function of pH on a chromaticity plot; (d) uptake of white PNPs functionalized with taurine; (e) an overlay of red, green and blue channels showing changes in fluorescent color; (f) a bar graph of different ratios showing sensitivity to changes in emission of white PNPs in different parts of the cell.
Figure 27:
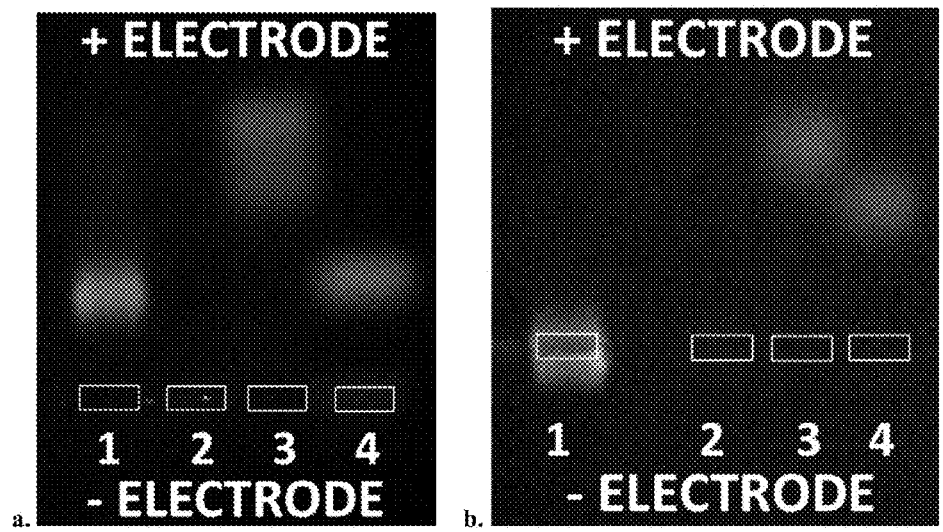
FIG. 27 shows agarose gels of: (a) nBSA$_{W254}$ (lane 1) and free M, F and R (lane 2-4, respectively) on a gel run in 40 mM Tris Acetate pH 7.0; and (b) the same samples on a gel run in 10 mM Tris Acetate pH 5.4.
Figure 28:
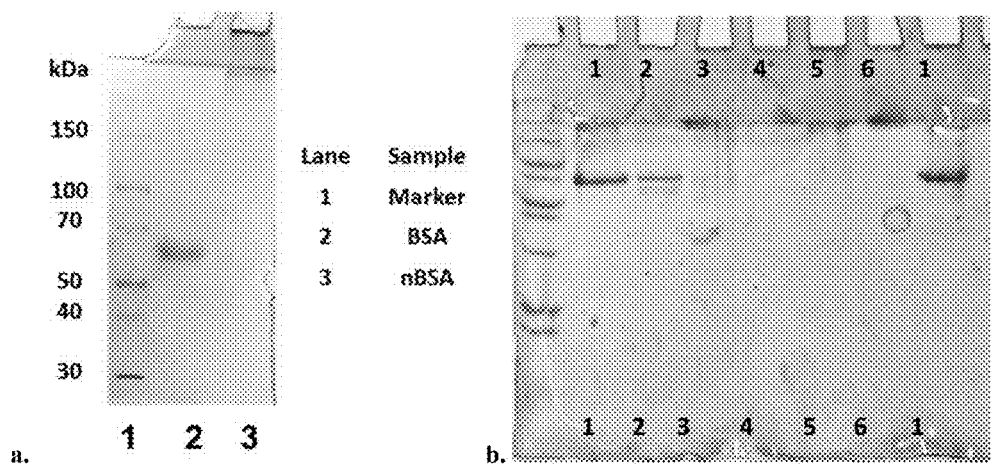
FIG. 28 shows: (a) 7% separate SDS gel showing that nBSA (lane 3) is composed of cross linked particles (smear at top of gel and protein still in well) with no free BSA (shown in lane 2 for comparison); (b) a 12.5% SDS-PAGE gel of BSA (lane 1), nBSA (lane 3), and nBSA$_{W254}$ (lane 5) and their respective products after 5 hours incubation with trypsin (lanes 2, 4, and 6 respectively).
Figure 29:
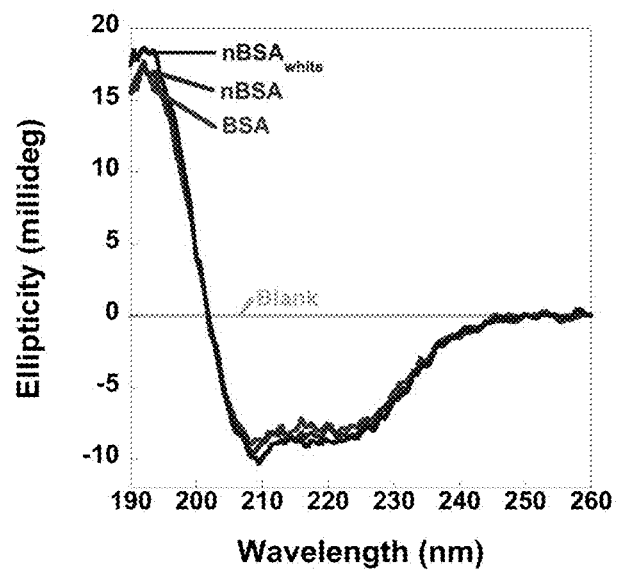
FIG. 29 shows CD spectra showing no loss in ellipticity for nBSA (red) and nBSA$_{W254}$ (blue) compared to BSA (black). All samples show double minima at 207 and 222 nm with one maximum at 195 nm. This spectral shape corresponds to an alpha helix structure.
Figure 30:
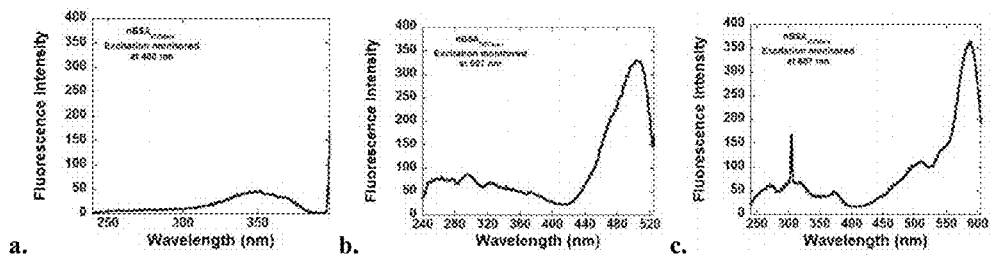
FIG. 30 shows excitation spectra of nBSA$_{W254}$ in 10 mM phosphate buffer pH 7.2 monitored at: (a) 400 nm; (b) 527 nm; and (c) 607 nm.
Figure 31:
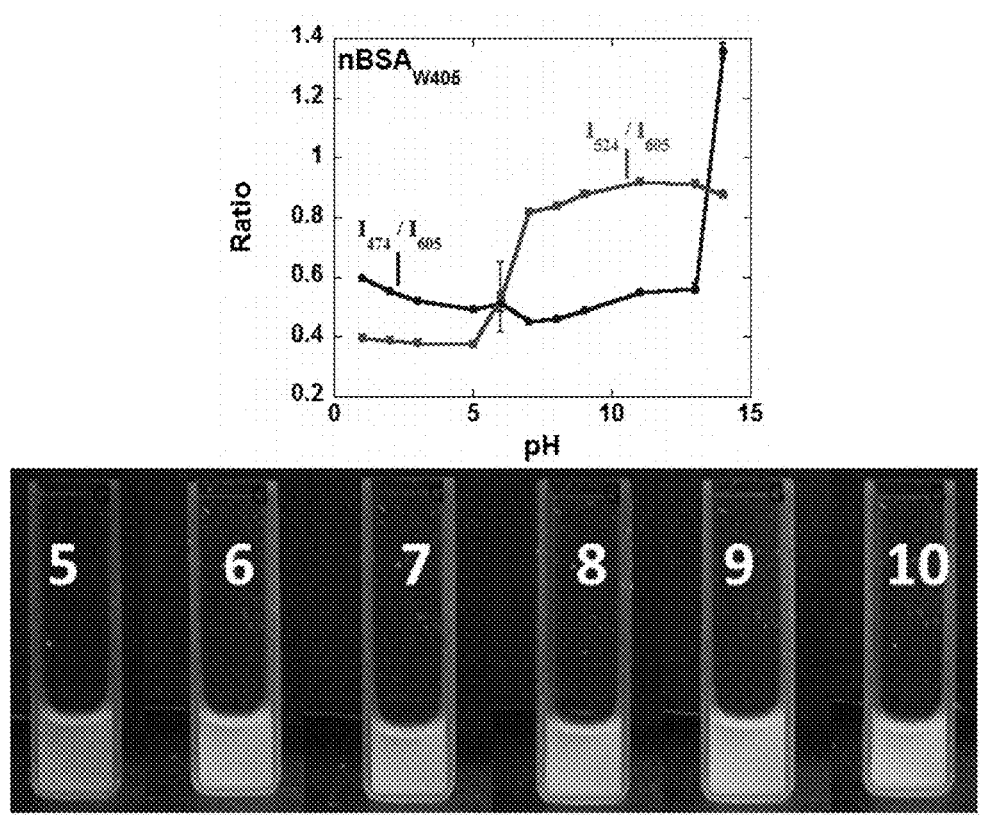
FIG. 31 shows: (top) a ratiometric sensitivity of nBSA$_{W405}$ to different pH values. Green line is the ratio of the intensity at 524 nm (F emission) to 605 nm (R emission). The blue line is the ratio of the intensity at 474 nm (D emission) to 605 nm (R emission); (bottom) a picture showing the change in emission color of particles as a function of pH. Solutions were imaged with a 365 nm light.
Figure 32:
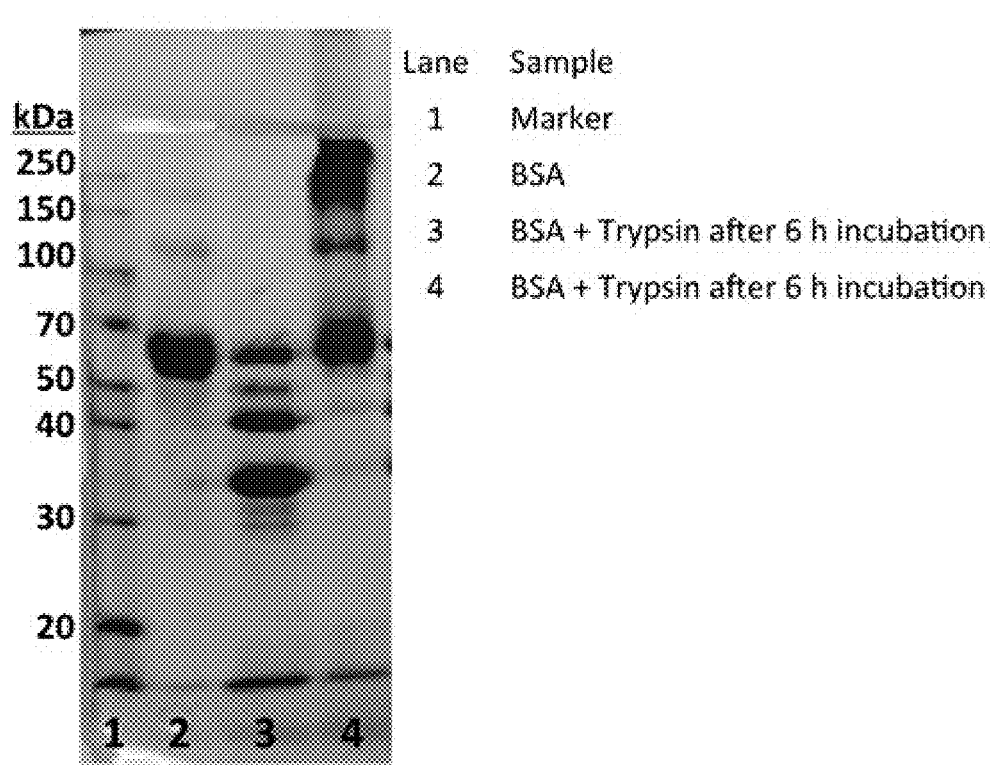
FIG. 32 shows an SDS PAGE gel of trypsin digestion products after 6 hours, using 12.5% separating gels and 4% stacking gels, run at 200 V for 30 minutes. Gels were stained once for 30 minutes, a second time for 30 minutes, and then were destained for 30 minutes, all with shaking. While BSA is showing significant peptide bands (bands below 66.5 kDa), much of the crosslinked protein of the nanoparticles remains in the well. It should be noted that particle was not purified of free protein previous to trypsin digestion so free protein was present in the sample.
Figure 33:
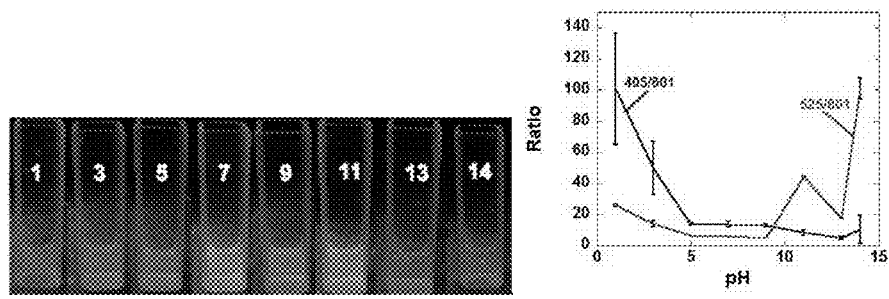
FIG. 33 shows color sensing of nBSA$_{W365}$ where all dyes are attached after synthesis of the protein nanoparticle.
Figure 34:
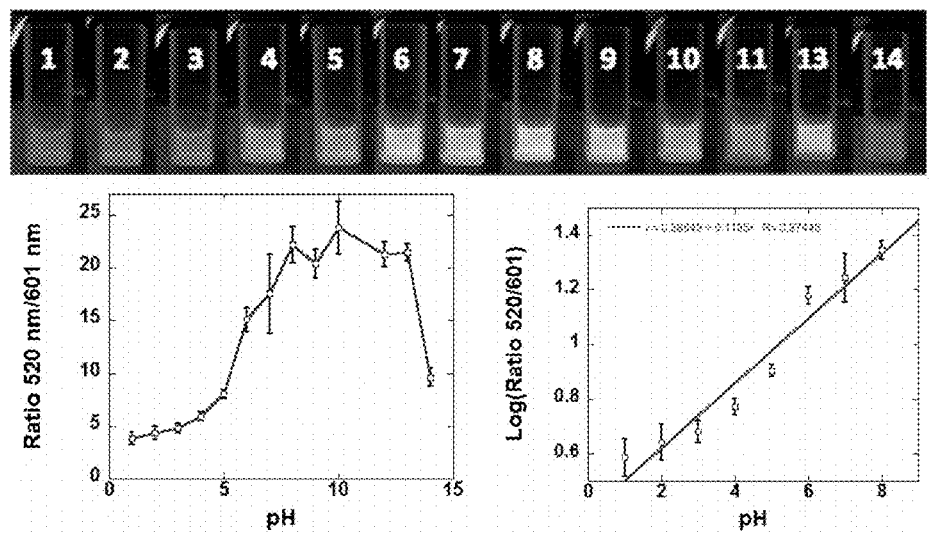
FIG. 34 shows color sensing of nBSA$_{W365}$ where the red dye is attached to the protein before synthesis of the nanoparticle (A) and the ratiometric response of the nanoparticles to pH (B).

As shown in FIG. 26, the white emission of the nBSAw254 particles at pH7 changed to purple at pH 1-2, yellow at pH 11, dull green at pH 13, and was nearly quenched at pH 14. The ratio of intensity of the 524 nm band to that of the 608 nm band versus pH was nearly linear from pH 4-11.

For cellular imaging, HeLa cells were incubated for 3 h, washed 3× with 10 mM phosphate buffer (pH 7.2) and imaged on a confocal fluorescence microscope. Separately, protease activity of the particles were tested and is demonstrated to be slow, and therefore it is likely that emission color is due to the particle environment and not hydrolysis of the particles on these time scales. See FIG. 26 for images.

Example 4. Additional GlowDots

A. nBSA-Au Nanoparticles

Figure 35:
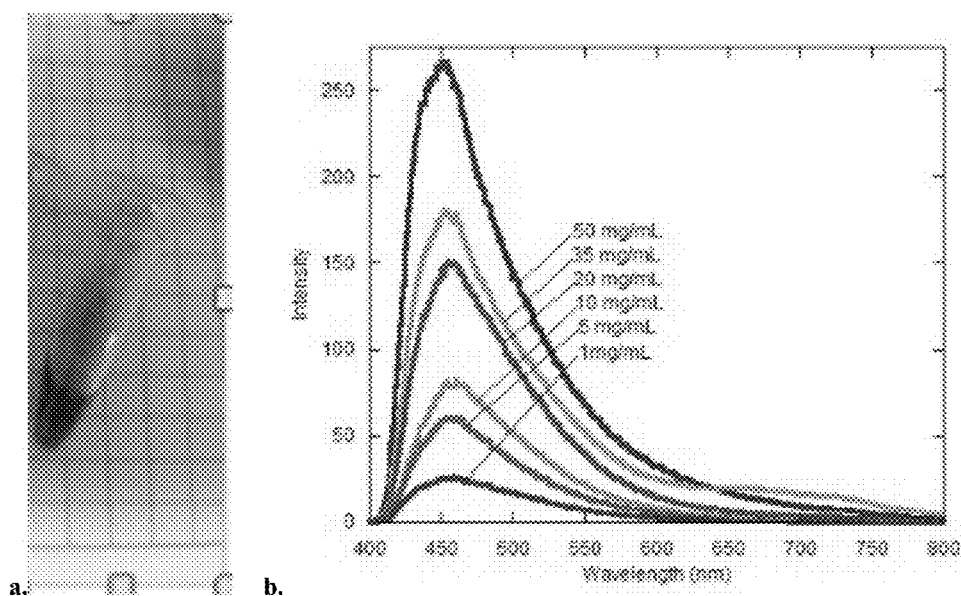
FIG. 35 shows: (A) an image of the final solution of nanoparticle containing Au nanoclusters (nBSAGold) where the nanoclusters were synthesized in the BSA after particle formation, where Au nanocluster presence is qualitatively confirmed by the purple color of the solution; (B) the fluorescence of the nanoparticle containing Au nanoclusters when excited at 360 nm, emission peak at 450 nm.

Gold BSA nanoparticle (nBSAGold) are synthesized in two ways, both of which use the same reagents. One way incorporates the gold nanoclusters into the BSA particles after they have already been formed. In this synthesis, one makes 1 mL of nBSA protein nanoparticles from 35 mg/mL BSA that have been crosslinked with 1M EDC and annealed at 80° C. After synthesis, the reaction is quenched with 15 mM carbonate buffer. At this point, 1.0 mL of 10 mM $HAuCl_4$ and 20 µL of 1M NaOH are added to the solution. It is then heated at 45° C. to form gold nanoclusters in the binding pocket of BSA. Solution color goes from yellow to red-purple as the particles form (see FIG. 35).

Figure 36:
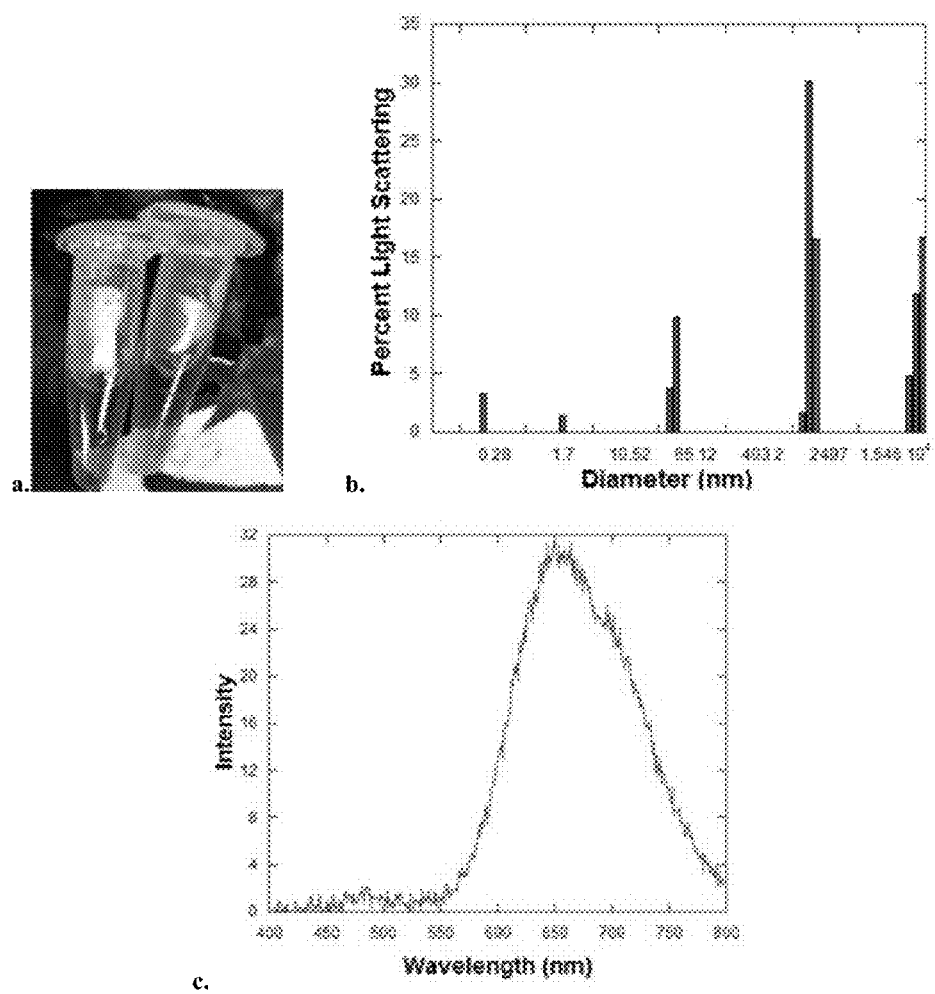
FIG. 36 shows: (A) an image the final solution of (nBSA-Gold) where the nanoclusters were synthesized in BSA before particle formation, where the presence of Au nanoclusters is confirmed by the purple color of the solution; (B) DLS data of protein nanoparticles containing Au nanoclusters; and (C) emission of (nBSAGold) when excited at 360 nm with emission peak at 650 nm.
Figure 37:
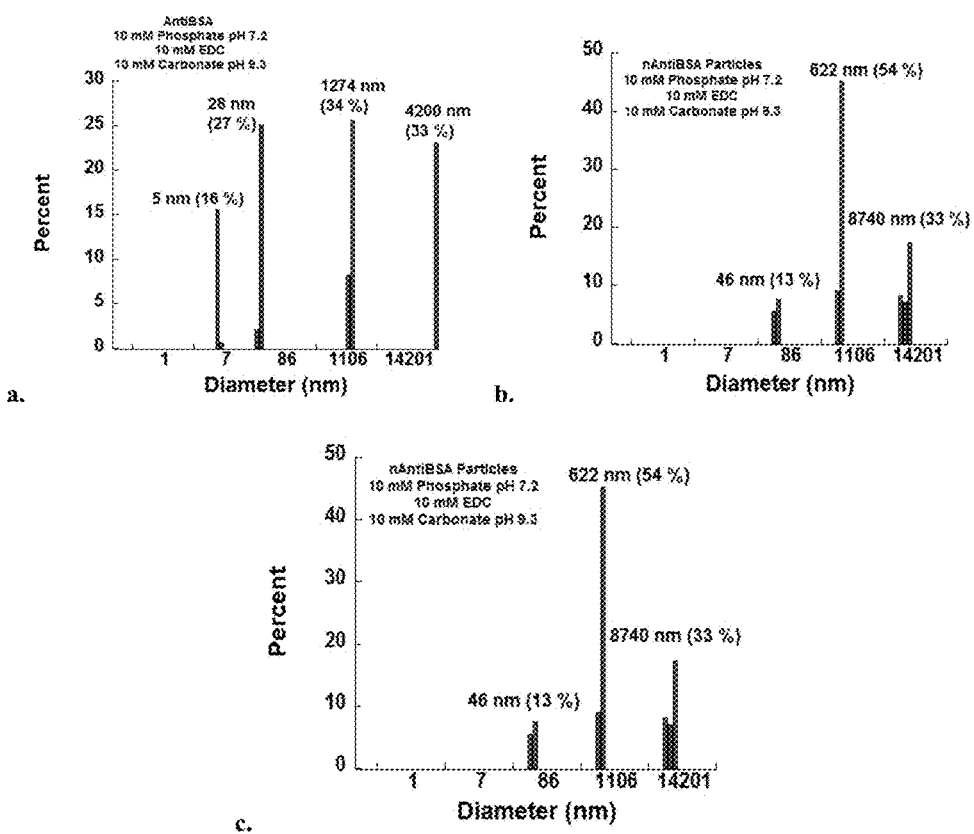
FIG. 37 shows DLS data demonstrating particle formation of antibodyBSA$_T$ via EDC crosslinking.
Figure 38:
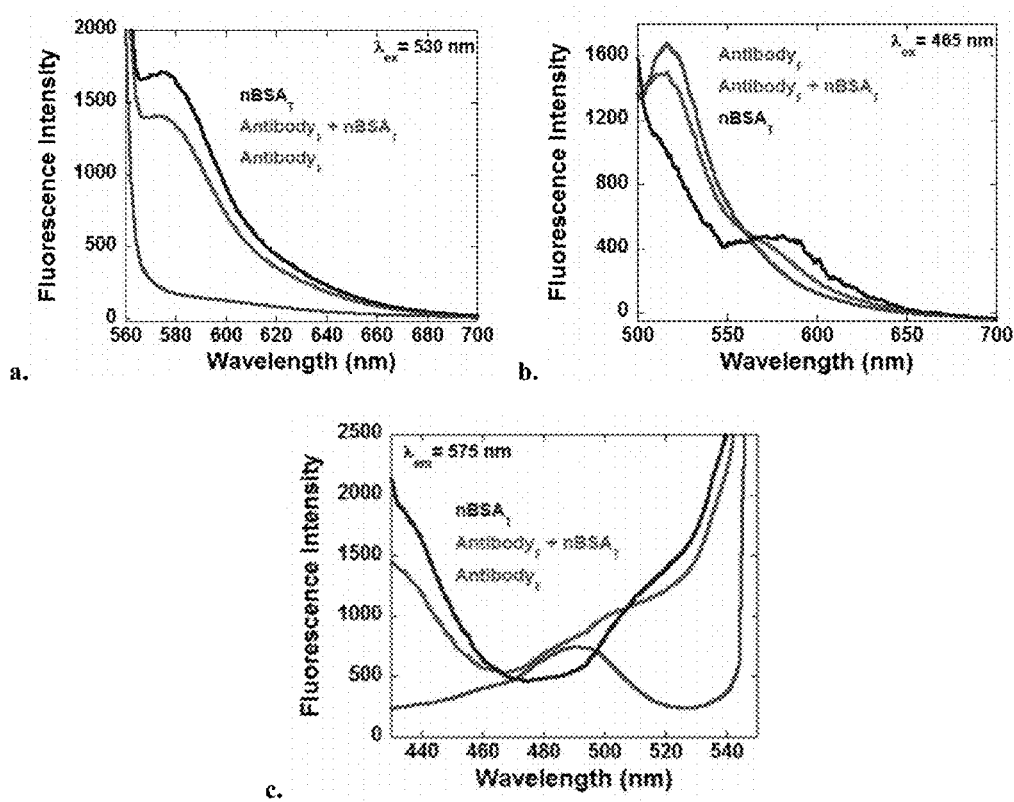
FIG. 38 shows detection of fluorescein labeled antibody with nBSA$_T$. Forster Resonance Energy Transfer (FRET) is used to confirm binding.
Figure 39:
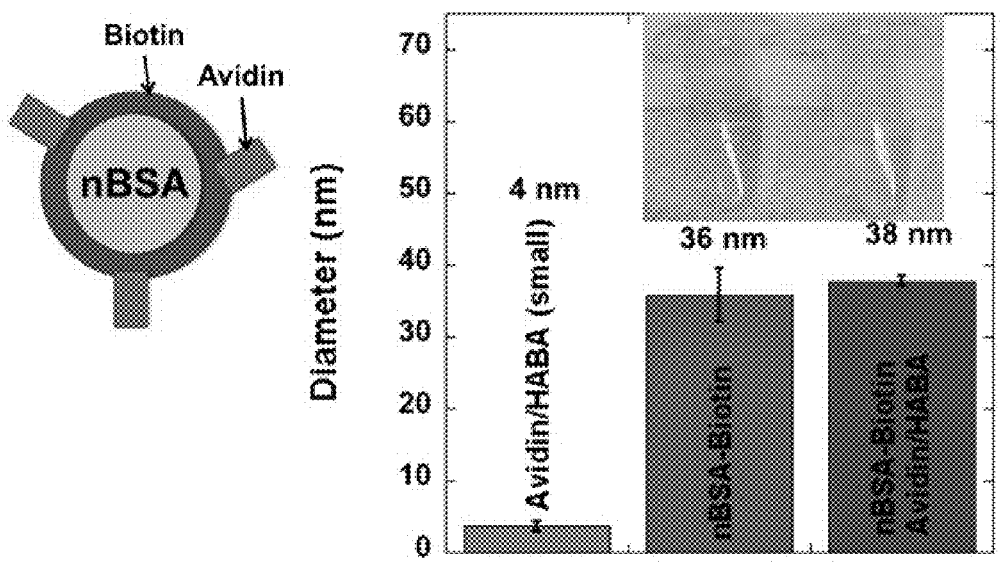
FIG. 39 shows results from an assay confirming biotinylation of nBSA particles, where a change in color of the sample from orange to yellow after addition of avidin/HABA indicates the presence of biotin.

The other way incorporates the gold nanoclusters into the BSA before protein nanoparticles are formed. In this method, 50 mg/mL BSA, 10 mM $HAuCl_4$, and 1 M NaOH are combined and then heated in a water bath for 12 hours at 45° C. to form Au-BSA. The solution changes from yellow to red as the particles form (see FIG. 36). Once the nanoclusters are made, 1M EDC is used to crosslink the particles together to form the nanoparticles.

The aforementioned particles synthesized both emit red fluorescence when excited with UV light. When using the first method, upon excitation at 360 nm, the emission peak is seen at 450 nm. We hypothesize that this is due to proximity of gold nanoclusters within the binding pockets of BSA. Using the second method, upon excitation at 360 nm, the emission peak is seen at 650.

These particles are fast and simple to synthesize. Depending on the method, one can change the fluorescent properties. Furthermore, these particles have several biological applications.

B. Synthesis of Antibody Particle of BSA Antibodies (nAb$_{BSA}$)

The nanoparticles of BSA antibody were synthesized by the addition of 10 mM EDC to 0.2 mg/mL antiBSA in 10 mM phosphate buffer pH 7.2. Reaction was stirred for 1 h and quenched with 2× sample volume of 10 mM Carbonate buffer pH 9.3. Particle growth was monitored by dynamic light scattering.

C. Synthesis of nBSA-Biotin nBSA was biotinylated using commercially available kit from Thermo Fisher Scientific (EZ Link NHS-PEG4 Biotinylation Kit, Product No. 21455). Biotinlyation was confirmed by the color change from orange to yellow upon the addition of Avidin/HABA reagent.

D. Detection of Antibodies with nBSA$_T$

Recognition of nBSA$_T$ by antiBSA antibody was determined by mixing 0.04 mg of FITC labeled BSA-antibody with 0.02 mg of nBSA$_T$. Binding was assessed by Forster resonance energy transfer (FRET) between the antibody and nBSA$_T$. Excitation spectra were collected while monitoring emission at 575 nm, and emission spectra collected while exciting at 465 or 530 nm to evaluate FRET.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. A method of synthesizing a white-emitting protein fluorescent nanoparticle, the method comprising:
    labeling a protein by covalent linkage with at least three different fluorescent dye reagents selected from the group consisting of fluoresceins, rhodamines, coumarins, pyrenes, cyanines, squaraines, and borondipyrromethenes; and
    crosslinking the protein with a crosslinking agent,
    to thereby form the white-emitting protein fluorescent nanoparticle, wherein the secondary structure of the protein is retained,
    wherein the protein is labeled with the fluorescent dyes either before or after the crosslinking step.

2. The method of claim 1, wherein the protein is labeled with the fluorescent dye reagent before the crosslinking step.

3. The method of claim 1, wherein the protein is labeled with the fluorescent dye reagent after the crosslinking step.

4. The method of claim 1, wherein the protein is selected from the group consisting of bovine serum albumin, glucose oxidase, horseradish peroxidase, catalase, lipase, hemoglobin, and lysozyme, and any combination thereof.

5. The method of claim 1, wherein the crosslinking agent is 1-ethyl-3-(3-dimethylaminopropyl) carbodiimide.

6. The method of claim 1, wherein the three fluorescent dye reagents are selected from the group consisting of: 1-pyrenebutanoic acid N-succinimidyl ester; 7-methoxycoumarin-3-carboxylic acid N-succinimidyl ester; 7-diethylaminocoumarin-3-carboxylic acid N-succinimidyl ester; fluorescein isothiocyanate; tetramethylrhodamine-5-(and-6)-isothiocyanate; and 5(6)-carboxy-X-rhodamine N-succinimidyl ester.

7. The method of claim 1, wherein the protein is bovine serum albumin, and the protein is labeled with three or four different fluorescent dye reagents selected from 7-methoxycoumarin-3-carboxylic acid N-succinimidyl ester, 7-diethylaminocoumarin-3-carboxylic acid N-succinimidyl ester, fluorescein isothiocyanate, and 5(6)-carboxy-X-rhodamine N-succinimidyl ester.

8. The method of claim 1, wherein the nanoparticle has a diameter in a range of about 10 nm to about 100 nm.

9. The method of claim 1, further comprising a step of annealing the nanoparticle by heating the nanoparticle to a temperature of about 80-90° C. for about 1-15 minutes.

10. The method of claim 1, wherein the nanoparticle emits white fluorescence upon excitation at about 254 nm or at about 405 nm, and wherein the white fluorescence emission has chromaticity coordinates in which x is about 0.30 to about 0.40 and y is about 0.30 to about 0.40.

11. The method of claim 1, further comprising a step of forming a metal nanocluster in the protein, either before or after the crosslinking step, wherein the metal is gold.

12. The method of claim 1, further comprising labeling the nanoparticle with a biological compound.

13. The method of claim 12, wherein the biological compound is selected from the group consisting of taurine and biotin.

14. The method of claim 1, wherein the nanoparticle has a particle size of about 10 nm to about 100 nm.

15. A method of synthesizing a white-emitting protein fluorescent nanoparticle, the method comprising:
    labeling a protein by covalent linkage with at least three different fluorescent dye reagents; and
    crosslinking the protein with a crosslinking agent,
    to thereby form the white-emitting protein fluorescent nanoparticle,
    wherein the protein is labeled with the fluorescent dyes either before or after the crosslinking step,
    wherein the three fluorescent dye reagents are selected from the group consisting of: 1-pyrenebutanoic acid N-succinimidyl ester; 7-methoxycoumarin-3-carboxylic acid N-succinimidyl ester; 7-diethylaminocoumarin-3-carboxylic acid N-succinimidyl ester; fluorescein isothiocyanate; tetramethylrhodamine-5-(and-6)-isothiocyanate; and 5(6)-carboxy-X-rhodamine N-succinimidyl ester.

16. A method of synthesizing a white-emitting protein fluorescent nanoparticle, the method comprising:
    labeling a protein by covalent linkage with at least three different fluorescent dye reagents; and
    crosslinking the protein with a crosslinking agent,
    to thereby form the white-emitting protein fluorescent nanoparticle,
    wherein the protein is labeled with the fluorescent dyes either before or after the crosslinking step,
    wherein the protein is bovine serum albumin, and the protein is labeled with three or four different fluorescent dye reagents selected from 7-methoxycoumarin-3-carboxylic acid N-succinimidyl ester, 7-diethylaminocoumarin-3-carboxylic acid N-succinimidyl ester, fluorescein isothiocyanate, and 5(6)-carboxy-X-rhodamine N-succinimidyl ester.

* * * * *